United States Patent
Boudreau et al.

(10) Patent No.: US 7,235,711 B2
(45) Date of Patent: Jun. 26, 2007

(54) PLANT CELL PLASTID TRANSFORMATION METHOD USING DUAL SELECTION AND PRODUCING TRANSPLASTOMIC PLANTS WITHOUT ANTIBIOTIC RESISTANCE GENES

(75) Inventors: Eric Boudreau, Research Triangle Park, NC (US); Weining Gu, Research Triangle Park, NC (US); Anic Deframond, Research Triangle Park, NC (US); Peter Heifetz, San Diego, CA (US)

(73) Assignee: Syngenta Participations AG, Basel (CH)

( * ) Notice: Subject to any disclaimer, the term of this patent is extended or adjusted under 35 U.S.C. 154(b) by 318 days.

(21) Appl. No.: 10/680,824

(22) Filed: Oct. 7, 2003

(65) Prior Publication Data

US 2004/0133937 A1 Jul. 8, 2004

Related U.S. Application Data

(60) Provisional application No. 60/425,331, filed on Nov. 12, 2002, provisional application No. 60/418,596, filed on Oct. 15, 2002.

(51) Int. Cl.
*C12N 15/82* (2006.01)
(52) U.S. Cl. .................................... 800/278
(58) Field of Classification Search ............... None
See application file for complete search history.

(56) References Cited

U.S. PATENT DOCUMENTS

| | | | | |
|---|---|---|---|---|
| 5,451,513 | A | 9/1995 | Maliga et al. | 800/278 |
| 6,084,155 | A | 6/2000 | Volrath et al. | 800/300 |
| 6,362,398 | B1 | 3/2002 | Heifetz et al. | 800/298 |
| 6,781,033 | B2 | 8/2004 | Staub et al. | 800/278 |
| 2002/0042934 | A1 | 4/2002 | Staub et al. | 800/300 |
| 2002/0073443 | A1 | 6/2002 | Heifetz et al. | 800/278 |

FOREIGN PATENT DOCUMENTS

| | | |
|---|---|---|
| WO | WO 97/32977 | 12/1997 |
| WO | WO 00/20612 | 4/2000 |
| WO | WO 00/39313 | 7/2000 |
| WO | WO 01/68826 A2 | 9/2001 |
| WO | WO 03/054189 | 7/2003 |
| WO | WO 03/054201 | 7/2003 |
| WO | WO 03/060137 | 7/2003 |

OTHER PUBLICATIONS

Kindle et al., *Engineering the Chloroplast Genome: Techniques and Capabilities for Chloroplast Transformation in Chlamydomonas Reinhardtii.* Proc. Natl. Acad. Sci. Mar. 1991, vol. 88, 1721-1725.
Bock, R., *Transgenic Plastids in Basic Research and Plant Biotechnology* Journal of Molecular Biology, vol. 312 (2001), pp. 425-438.

Bogorad, L., *Engineering chloroplasts: an alternative site for foreign genes, proteins, reactions and products* Trends in Biotechnology, vol. 18 (2000), pp. 257-263.
Boudreau et al., *A large open reading frame (orf1995) in the chloroplast DNA of Chlamydomonas reinhardtii encodes an essential protein* Molecular and General Genetics, vol. 253 (1997), pp. 649-653.
Boynton et al., *Chloroplast transformation in Chlamydomonas with high velocity microprojectiles* Science, vol. 240 (1988), pp. 1534-1537.
Carrer et al., *Targeted insertion of foreign genes into the tobacco plastid genome without physical linkage to the selectable marker gene* Biotechnology, vol. 13 (1995) pp. 791-794.
Carrer et al., *Kanamycin resistance as a selectable marker for plastid transformation in tobacco* Molecular and General Genetics vol. 241 (1993), pp. 49-56.
Corneille et al., *Efficient elimination of selectable marker genes from the plastid genome by the CRE-lox site-specific recombination system* The Plant Journal, vol. 27 (2001) pp. 171-179.
Daniell et al., *Containment of herbicide resistance through genetic engineering of the chloroplast genome* Nature Biotechnology, vol. 16 (1998) pp. 345-348.
Daniell et al., *Marker free transgenic plants: engineering the chloroplast genome without the use of antibiotic selection* Current Genetics, vol. 39 (2001) pp. 109-116.
Doetsch et al., *Chloroplast transformation in Euglena gracilis: slicing of a group III twintron transcribed from a transgenic psbK operon* Current Genetics, vol. 39 (2001) pp. 49-60.
Drescher et al., *The two largest chloroplast genome-encoded open reading frames of higher plants are essential genes* Plant Journal, vol. 22 (2000) pp. 97-104.
Fischer et al., *Selectable marker recycling in the chloroplast* Molecular and General Genetics, vol. 251, (1996) pp. 373-380.
Hajdukiewicz et al., *Multiple pathways for Cre/lox-mediated recombination in plastics* The Plant Journal, vol. 27 (2001) pp. 161-170.
Heifetz, P.B., *Genetic engineering of the chloroplast* Biochimie, vol. 82 (2000) pp. 655-666.
Hou et al., *Chloroplast transformation in oilseed rape* Transgenic Research, vol. 12 (2003), pp. 111-114.
Huang et al., *The Chlamydomonas chloroplast clpP gene contains translated large insertion sequences and is essential for cell growth* Molecular and General Genetics, vol. 244 (1994) pp. 151-159.
Iamtham and Day, *Removal of antibiotic resistance genes from transgenic tobacco plastids* Nature Biotechnology, vol. 18 (2000), pp. 1172-1176.

(Continued)

*Primary Examiner*—Anne Kubelik

(57) ABSTRACT

The present invention relates to the field of plastid transformation. The invention provides transformation vectors and methods to obtain transplastomic plants or algae having a transformed plastid comprising the steps of introducing into plastids a recombinant nucleic acid molecule or vector, and two phases of selection with first selection phase using a non-lethal compound and a second selection phase using a lethal compound. Alternatively, the dual selection method is conducted simultaneously using a lower concentration of the lethal compound.

11 Claims, 7 Drawing Sheets

OTHER PUBLICATIONS

Knoblauch et al., *A galinstan expansion femtosyringe for microinjection of eukaryotic organelles and prokaryotes* Nature Biotechnology, vol. 17 (1999), pp. 906-909.

Kofer et al., *PEG-mediated plastid transformation in higher plants* In Vitro Cellular and Developmental Biology—Plant, vol. 34 (1998), pp. 303-309.

Koop et al., *Integration of foreign sequences into the tobacco plastome via polyethylene glycol-mediated protoplast transformation* Planta, vol. 199 (1996), pp. 193-201.

Lapidot et al., *Stable chloroplast transformation of the unicellular red alga Porphyridium species* Plant Physiology, vol. 129 (2002), pp. 7-12.

Lutz et al., *Expression of bar in the Plastid Genome Confers Herbicide Resistance* Plant Physiology, vol. 125 (2001), pp. 1585-1590.

O'Neill et al., *Chloroplast transformation in plants: polyethylene glycol (PEG) treatment of protoplasts is an alternative to biolistic delivery systems* Plant Journal, vol. 3 (1993), pp. 729-738.

Ruf et al., *Stable genetic transformation of tomato plastids and expression of a foreign protein in fruit* Nature Biotechnology, vol. 19 (2001) pp. 870-875.

Shikanai et al., *The chloroplast clpP gene, encoding a proteolytic subunit of ATP-dependent protease, is indispensable for chloroplast development in tobacco* Plant Cell Physiology, vol. 42 (2001), pp. 264-273.

Sidorov et al., *Stable chloroplast transformation in potato: use of green fluorescent protein as a plastid marker* The Plant Journal, vol. 19(2) (1999), pp. 209-216.

Sikdar et al., *Plastid transformation in Arabidopsis thaliana* Plant Cell Reports, vol. 18 (1991), pp. 20-24.

Skarjinskaia et al., *Plastid Transformation in Lesquerella Fendleri, an Oilseed Brassicacea* Transgenic Research, vol. 12 (2003), pp. 115-122.

Staub, J. and Maliga, P., *Long Regions of Homologous DNA Are Incorporated into the Tobacco Plastid Genome by Transformation* The Plant Cell, vol. 4 (Jan. 1992), pp. 39-45.

Svab, et al, *High-frequency plastid transformation in tobacco by selection for chimeric aadA gene* Proceedings of the National Academy of Science, USA, vol. 90 (1993), pp. 913-917.

Svab et al., *Stable Transformation of Plastids in Higher Plants* Proceedings of the National Academy of Science, USA, vol. 87 (1990) pp. 8526-8530.

Ye et al., *Persistence of Unselected Transgenic DNA during a Plastid Transformation and Segregation Approach to Herbicide Resistance* Plant Physiology, vol. 133 (2003), pp. 402-410.

Ye et al., *Plastid-expressed 5-enolpyruvylshikimate-3-phosphate synthase genes provide high level glyphosate tolerance in tobacco* The Plant Journal, vol. 25(3) (2001), pp. 261-270.

PLANT CELL PLASTID TRANSFORMATION METHOD USING DUAL SELECTION AND PRODUCING TRANSPLASTOMIC PLANTS WITHOUT ANTIBIOTIC RESISTANCE GENES

This application is a non-provisional application of provisional application No. 60/425,331 filed Nov. 12, 2002.

This application claims the benefit of U.S. Provisional Application No. 60/418,596 filed Oct. 15, 2002, which is incorporated by reference in its entirety.

FIELD OF THE INVENTION

The present invention relates to the field of plastid transformation. The invention provides transformation vectors and methods to obtain transplastomic plants or or algae having a transformed plastid comprising the steps of introducing into plastids a recombinant nucleic acid molecule or vector, and two phases of selection with first selection phase using a non-lethal compound and a second selection phase using a lethal compound. Alternatively, the dual selection method is conducted simultaneously, using a lower concentration of the lethal compound.

BACKGROUND OF THE INVENTION

Improvement of plant varieties through transformation has become increasingly important for modern plant breeding. Various gene transfer technologies allow the incorporation of foreign DNA molecules into plants genomes. The expression of genes encoded by such foreign DNA molecules (transgenes, genes of interest) can potentially confer new beneficial characteristics to the plant like, for example, improved crop quality or yield. The expression of transgenes can also allow for the use of plants as bioorganic factories.

Most gene transfer systems, such as *Agrobacterium*-mediated transformation or bombardment with DNA-coated particles, stably integrate heterologous genes in the nuclear genome of the plant by means of non-homologous recombination. Plant engineering using these methods has several drawbacks. These methods produce a population of transformants varying in their transgene copy number and whose expression is often unpredictable because of position effect variations or possible gene silencing. Most transgenic plants produced by these methods contains within their nuclear genome non-desired vector sequences associated with the gene of interest. Furthermore, the threat of transgene contamination of wild relative plants from genetically modified plant is a major environmental concern. The risk of transgene escape from genetically altered crops to wild relatives predominantly arises through pollen dissemination.

Plastid gene transformation is an important alternative for the expression of heterologous genes in plants (reviewed by Bogorad, Trends Biotechnol. 18: 257–263, 2000 and Bock, J. Mol. Biol. 312: 425–438, 2001). Although plastid genomes are relatively small in size, 120 to 160 kb, they can easily accommodate several kilo bases of foreign DNA within them. Insertion of foreign DNA in the plastid genome mainly occurs via homologous recombination and a transgene can be site directed at a particular locus using suitable homologous flanking regions. One of the major advantages of plastid transformation is that it is possible to obtain very high transgene expression. The plastid genome (plastome) is highly polyploid so the transgene is expressed from multiple gene copies in the plastid. The polyploidy of the plastid genome is such that a mature leaf cell may contain over 10,000 copies of the plastome. Also contributing to the high level of the plastid transgene expression is absence of position effect and gene silencing. Another major advantage is that plastids from most crop plants are only maternally inherited and thus, the ecological risk of plastid transgene escape through pollen-mediated out crossing is minimized. The basic DNA delivery techniques for plastid transformation are either via particle bombardment of leaves or polyethylene glycol mediated DNA uptake in protoplasts. Plastid transformation via biolistics was initially achieved in the unicellular green alga *Chlamydomonas reinhardtii* (Boynton et al., Science 240: 1534–1537, 1988) and this approach, using selection for cis-acting antibiotic resistance loci (spectinomycin/streptomycin resistance) or complementation of non-photosynthetic mutant phenotypes, was extended to *Nicotiana tabacum* (Svab et al., Proc. Natl. Acad. Sci. USA 87: 8526–8530, 1990), Arabidopsis (Sikdar et al., Plant Cell Reports 18:20–24, 1991), *Brassica napus* (WO 00/39313), potato (Sidorov et al., The Plant Journal 19(2):209–216, 1999), petunia (WO 00/28014), tomato (Ruf et al., Nature Biotechnology 19: 870–875, 2001), oilseed rape (Hou et al., Transgenic Res. 12: 111–114, 2003) and *Lesquerella Fendleri*(Skaijinskaia et al., Transgenic Res. 12: 115–122, 2003). Plastid transformation of protoplasts from tobacco and the moss *Physcomitrella patens* has been attained using polyethylene glycol (PEG) mediated DNA uptake (O'Neill et al., Plant J. 3: 729–738, 1993; Koop et al., Planta 199: 193–201, 1996). More recently, micro-injection of DNA directly in plastids of marginal mesophyll cells of intact tobacco plant resulted in transient expression (Knoblauch et al., Nature Biotechnology 17: 906–909, 1999) but stable transformants using this technique have yet to be reported. Stable chloroplast transformation by biolistics was also reported for the Euglenophyte *Eugena gracilis* (Doetsch et al., Curr Genet. 39:49–60, 2001) and the unicellular red alga *Porphyridium* sp. (Lapidot et al., Plant Physiol. 129: 7–12, 2002), the dominant selectable marker used for latter consist of a mutant form of the gene encoding acetohydroxyacid synthase which confers tolerance to the herbicide sulfometuron methyl. As previously mentioned, chloroplast transformation consists of integrating a foreign DNA at a precise position in the plastid genome by homologous recombination. The plastid transformation vectors consist of cloned plastid DNA, homologous to the targeted region, which flanks a selectable marker gene which itself is linked to a gene or several genes of interest. After transformation, the transgene(s) and the selectable marker are inserted together as a block of heterologous sequence in the targeted locus of the plastid genome via homologous recombination between the vectors plastid sequence and the targeted locus. In order to obtain stably transformed homoplasmic plants, i.e. plants having the foreign DNA inserted into every plastome copy of the plant cell, several rounds of subculture on selective media are required. This process facilitates the segregation of transplastomic and untransformed plastids and results in the selection of homoplasmic cells with gene(s) of interest and the selectable marker stably integrated into the plastome, since these genes are linked together.

Most stable plastid transformation demonstrated to date has been based on selection using the antibiotic resistance gene aadA (as referenced above) or NPTII (Carrer et al., Mol Gen Genet 241:49–56, 1993), to obtain homoplasmic plants. These selectable markers confer a specific selection phenotype, the green pigmentation (U.S. Pat. No. 5,451,513), which allows to visually distinguish the green pigmented transplastomic cells from cells having wild-type plastids which are non pigmented under selection conditions.

Most plastid transformation methods rely on the use of a selectable marker that confers a non-lethal selection. These selectable markers also confer a specific selection phenotype, the green pigmentation (U.S. Pat. No. 5,451,513) which allows one to visually distinguish the green pigmented transplastomic cells from cells having wild-type plastids that are non-pigmented under selection conditions. For example, plants transformed with the bacterial aadA gene which confers resistance to spectinomycin and streptomycin grow normally in the presence of either one of these antibiotics whereas untransformed plants are bleached. Transformed plants can thus easily be identified using chlorophyll as a visual marker. There is a limited number of selectable markers available for plastid transformation and the most reliable ones, such as aadA or point mutations in the plastid 16S rDNA and rps12 genes, confer resistance to the same antibiotics, spectinomycin and/or streptomycin. Selectable markers conferring resistance to other antibiotics such as kanamycin were shown to be much less effective for plastid transformation.

There have been concerns on the antibiotic resistance genes in genetically modified (GM) crops because of the potential risks of horizontal gene transfer to micro organisms in the environment or to gut microbes. These potential risks may pose even greater concerns with transplastomic plants because of the prokaryotic characteristics of the plastid genome and the by far larger copy number of the transgene per cell. It is therefore highly desirable to obtain transplastomic plants without antibiotic resistance genes.

Another alternative are methods wherein the antibiotic resistance gene is removed after the transformation. Once plants are homoplasmic for the transgene, the presence of the selectable marker gene in the plastome is no longer required. Removal of the selectable marker from a transplastomic plant has been achieved by two different methods. The first method, initially developed for recycling of the selectable marker from a transformed *C. reinhardtii* plastome (Fischer et al., Mol. Gen. Genet. 251:373–80, 1996) and recently extended to *Nicotiana tabacum* (Iamtham and Day, Nat. Biotechnol. 18: 1172–1176, 2000), relies on the plastid homologous recombination system to delete the marker gene from the plastid genome. Homologous recombination between direct repeated sequences flanking the selectable marker results in the deletion of the DNA segment. This method requires several rounds of self- or backcrossing before transgenic plants without the selectable marker are obtained. The second method uses the Cre/lox recombination system (Hajdukiewicz et al., The Plant J. 27: 161–170, 2001; Corneille et al., The Plant J. 27: 171–179, 2001) to excise the DNA segment. In this method the Cre-protein mediates the excision of a DNA segment located between two lox sites in direct repeat orientation. In order to remove the selectable marker, the Cre gene is introduced into the nuclei of the transplastomic plants either through nuclear transformation or through crossing. Once the selectable marker gene is removed, the Cre gene is eliminated by genetic crossing. Albeit successful, removal of the selectable marker using either one of these methods have some disadvantages. Both methods are lengthy processes as multiple rounds of crossing may be required, and both methods leave an undesired residual heterologous DNA segment in the plastid genome that serves no purpose. Furthermore, unspecific recombination causing DNA deletions was observed with Cre/lox recombination system (Hajdukiewicz et al., 2001). Thus, there is a need to develop other methods to obtain transplastomic plants without the stable integration of an antibiotic selectable marker in the plastid genome.

The application of antibiotic resistance genes as the selectable marker for plastid transformation is also limited by the requirement of the green pigmentation as the selection phenotype. A selection based on green pigmentation needs to be carried out in the light, which may not be the optimal culture condition for some plant cell cultures. Furthermore, not all the tissue types exhibit the green pigmentation phenotype under normal culture conditions, such as most of the cell cultures from cereal crops. It is therefore desirable to develop a selection strategy for plastid transformation in which the selection is not dependent on the green pigmentation.

Certain non-antibiotic resistance marker genes, such as the protoporphyrinogen oxidase gene (U.S. Pat. No. 6,084,155), 5-enolpyruvylshikimate-3-phosphate synthase genes (Daniell et al., Nature Biotech 16:345–348, 1998; Ye et al., The Plant Journal 25(3):261–270, 2001), and the bar gene (Lutz et al., Plant Physiology 125:1585–1590, 2001), can be effectively expressed in transplastomic plants. Most recently, EPSPS and bar gene are also reported being used in segregation approach to obtain herbicide resistant transplastomic plants with exclusion of antibiotic gene (Ye et al., Plant Physiology 133:402–410, 2003).

Another alternative is using the spinach betaine aldehyde dehydrogenase as the selectable marker that confers resistance to the lethal compound betaine aldehyde (Daniell et al., Curr Genet 2001 39:109–116, 2001).The present invention provides methods for plastid transformation in a wide variety of plant species and algae. It addresses the problem of removal of the antibiotic resistance marker which is delivered to the plastids during transformation and provides selection methods for homoplasmic transplastomic plants wherein green pigmentation of the selected phenotype is not a prerequisite.

SUMMARY OF THE INVENTION

One embodiment of the invention is a method for obtaining a transplastomic plant comprising the steps of: A method for obtaining a transplastomic plant comprising the steps of:
  a) introducing into a plant cell plastid a recombinant nucleic acid molecule comprising two distinct selectable marker constructs, wherein the first marker confers resistance to a non-lethal selective compound (non-lethal marker) and the second marker confers tolerance to a lethal compound (lethal marker) and wherein each of the selectable marker constructs comprises a promoter functional in a plant cell plastid and a transcriptional termination region functional in a plant cell plastid
  b) placing the plant cell comprising the recombinant nucleic acid molecule on a first culture medium comprising a plastid non-lethal compound for either 1) a period of about 2 weeks or 2) or until shoots appear on a callus formed from the plant cell;
  c) placing the plant cell on a second culture medium comprising a plastid lethal compound for a period of time sufficient to permit the plant cell to be homoplasmic for the transgene.

In another embodiment, the method further comprises the step of: d) obtaining a transplastomic plant comprising only the second, lethal marker.

The method of claim 1, wherein the recombinant nucleic acid molecule further comprises one or more constructs of gene products of interest expressible in plastids are adjacent to the lethal marker.

In another embodiment the lethal marker and the gene construct are organized as a operon-like polycistronic gene.

In a preferred embodiment of the invention the introduction of the recombinant nucleic acid molecule is accomplished by a plastid transformation vector, said vector comprising the recombinant nucleic acid molecule encoding the non-lethal marker in its backbone sequence and the nucleic acid molecule encoding the lethal marker flanked by nucleic acid sequences which are homologous to non-essential plastid nucleic acid sequences.

In another preferred embodiment of the invention the delivery of the recombinant nucleic acid molecule encoding the markers is accomplished by a plastid transformation vector, said vector comprising the recombinant nucleic acid molecule encoding the non-lethal marker flanked by DNA sequences which are homologous to essential plastid DNA sequences and the nucleic acid molecule encoding the lethal marker flanked by nucleic acid sequences which are homologous to non-essential plastid nucleic acid sequences.

In another preferred embodiment the vector is transiently integrated into the plastome.

In another preferred embodiment a nucleic acid molecule encoding the non-lethal marker is unstably integrated into the plastome.

In another embodiment, the selected phenotype does not depend on the green pigmentation of the plastids.

In a preferred embodiment of the invention, the non-lethal marker is an antibiotic resistance gene. More preferably, the antibiotic resistance gene is aadA and the non-lethal selective compound is spectinomycin.

In another preferred embodiment of the invention, the lethal marker is a herbicide tolerance gene. More preferably, the herbicide tolerance gene is a mutated form of a protoporphorynogen oxidase (PPO) and the lethal selective compound is butafenacil or Formula XVII.

In a more preferred embodiment of the invention a plastid transformation vector comprises SEQ ID NO: 1, SEQ ID NO:2, SEQ ID NO:3 or SEQ ID NO:19.

In another embodiment, the invention is a plastid transformation vector comprising a non-lethal marker flanked by sequences homologous to essential plastid DNA sequences but no non-lethal marker flanked by DNA sequences homologous to nonessential plastid DNA sequences. Preferably, the plastid transformation vector comprises SEQ ID NO:3.

In preferred embodiments of the invention the transformed plant cell or plant derived therefrom is tobacco, tomato, potato, brassica spp., safflower or lemna.

Another embodiment of the invention is a plastid transformation vector comprising a non-lethal marker in the backbone sequence of the vector and a lethal marker flanked by sequences which are homologous to non-essential plastid DNA sequences.

A preferred embodiment of the invention is a plastid transformation vector comprising SEQ ID NO:1 or SEQ ID NO:2.

Another embodiment of the invention is a method of producing a homoplasmic transplastomic plant comprising:
a) delivery of a DNA fragment encoding at least two distinct selectable markers to plant plastids and expression of said markers in the plant plastids, wherein the first marker is conferring resistance to a non-lethal selective compound (non-lethal marker) and the second marker is conferring tolerance to a lethal compound (lethal marker),
b) a first round of selection using the non-lethal selective compound alone or in combination with the lethal selective compound for selection of transplastomic events,
c) a second round of selection using the lethal compound as the sole selective compound such that the non-lethal marker gene is removed from the plastome, and
d) selection of homoplasmic transplastomic events using the lethal compound as the sole selective compound, wherein the selected events have the lethal marker but not the non-lethal marker integrated into their plastome.

The method may further comprise the step of E) obtaining a transplastomic plant comprising only the lethal marker.

Another embodiment of the invention is a homoplasmic transplastomic plant produced by a this method.

A method for obtaining a chloroplast transformed algae comprising the steps of:
a) introducing into a plastid of a an algae a recombinant nucleic acid molecule encoding at least two distinct selectable markers expressible in plastids, wherein the first marker confers resistance to a non-lethal selective compound (non-lethal marker) and the second marker is conferring tolerance to a lethal compound (lethal marker) and wherein;
b) a first round of selection using the non-lethal selective compound alone or in combination with the lethal selective compound for selection of a transformed plastid; and
c) a second round of selection using the lethal compound as the sole selective compound such that the non-lethal marker gene is removed from the plastome.

Preferably, the algae is a *Chlamydomonas* spp., a red algae or a green algae.

The invention relates to a method of obtaining a transplastomic plant comprising the steps of
a) introducing into a plant cell plastid a recombinant nucleic acid molecule comprising two distinct selectable marker constructs, wherein the first marker confers resistance to a non-lethal selective compound (non-lethal marker) and the second marker confers tolerance to a lethal compound (lethal marker) and wherein each of the selectable marker constructs comprises a promoter functional in a plant cell plastid and a transcriptional termination region functional in a plant cell plastid
b) placing the plant cell comprising the recombinant nucleic acid molecule on a first culture medium comprising a plastid non-lethal compound and a lethal compound for 1) a period of about 2 weeks or 2) until shoots appear on a callus formed from the plant cell;
c) placing the plant cell on a second culture medium comprising a plastid lethal compound for a period of time sufficient to permit the plant cell to be homoplasmic for the transgene.

Preferably, wherein the lethal compound is a herbicide and the non-lethal compound is an antibiotic.

More preferably, wherein the lethal compound is butafenacil or Formula XVII and the antibiotic is spectinomycin or streptomycin.

The invention also related to the method, wherein the concentration of the lethal compound is less than about 10 nM or wherein the concentration of the lethal compound is between about 5 nM and about 25 nM; or wherein the concentration of the lethal compound is between about 25 nM and about 50 nM.

DESCRIPTION OF SEQUENCE LISTING

Figure 1:
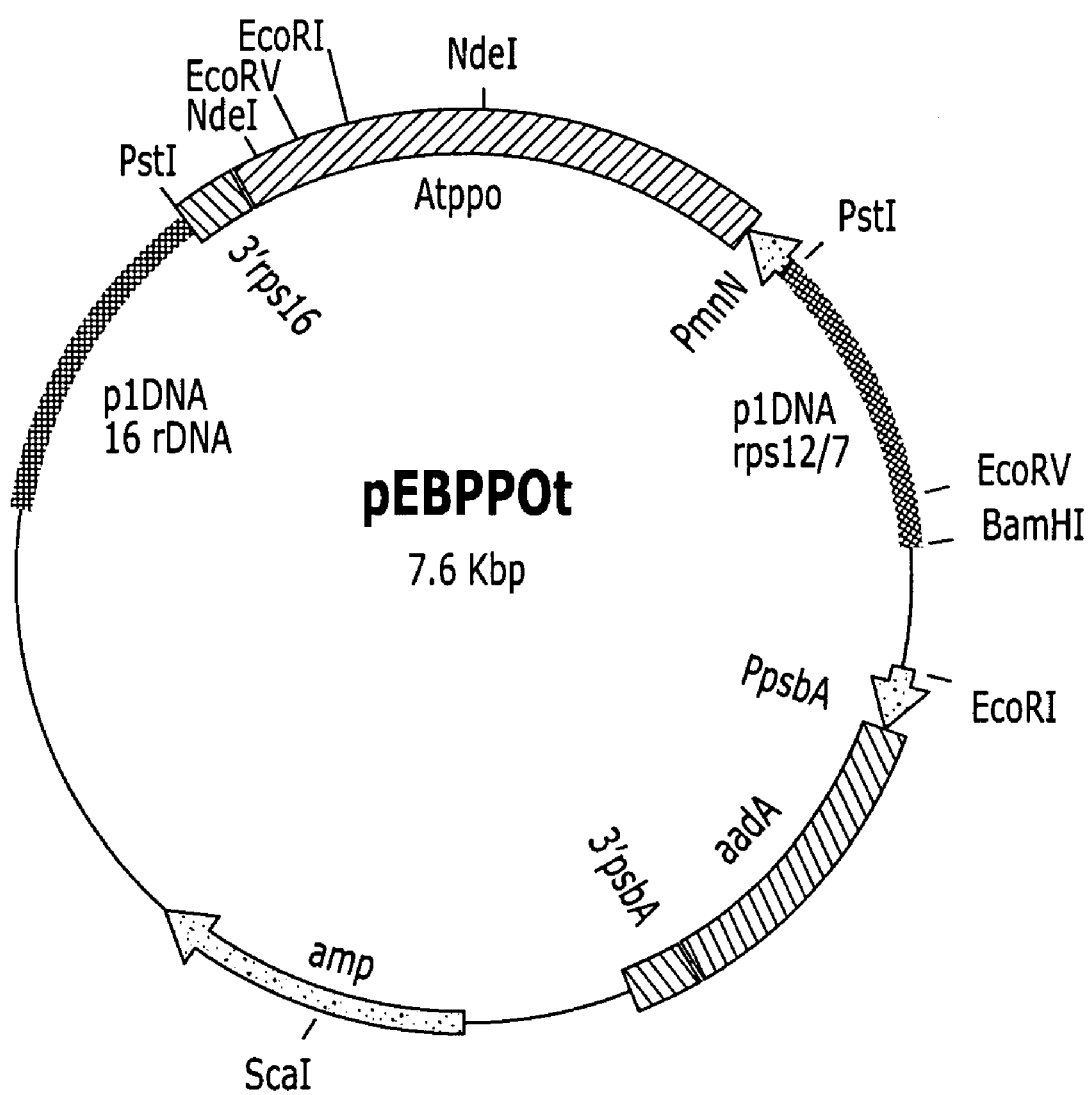
FIG. 1. Map of the pEBPPOt plastid transformation vector (SEQ ID NO:1). Plastid targeting sequence plDNA 16rDNA and rps12/7 are represented by hatched lines. Components of the chimeric *A. thaliana* ppo gene are the maize plastid 16S PEP-NEP rRNA gene promoter fused to the *N. tabacum* plastid rbcL RBS (SEQ ID NO:4; PmrrN), the *A. thaliana* ppo gene (Atppo) and the *N. tabacum* plastid rps16 3'UTR (3'rps16). Components of the chimeric aadA gene are *N. tabacum* psbA promoter (PpsbA) fused to aadA, aadA coding sequence (aadA) and the *A. thaliana* psbA 3'UTR (3'psbA). The ampicilline resistance on the vector backbone sequence (amp) is encoded by the bla gene and indicated by an arrow. The restriction sites are marked for: PstI, NdeI, EcoRI, EcoRV, BamHI and ScaI.

SEQ ID NO:1 pEBPPOt plastid transformation vector (Example 1 VII).

SEQ ID NO:2 pEB8 (=pEB8a) plastid transformation vector (Example 2).

SEQ ID NO:3 pNY2C plastid transformation vector (Example 4 II).

SEQ ID NO:4 DNA sequence of the maize plastid 16S PEP-NEP rRNA gene promoter fused to the *N. tabacum* plastid rbcL ribosome binding site (RBS).

SEQ ID NO:5 Top primer for amplification of the 16S PEP-NEP rRNA gene promoter from maize plastid DNA, the primer comprising an EcoRI restriction site (Example 1 I).

SEQ ID NO:6 Bottom primer comprising a BspHI restriction site (Example 1 I).

SEQ ID NO:7 Top primer for amplification of the *A. thaliana* ppo gene (Example 1 II).

SEQ ID NO:8 Bottom primer for amplification of the *A. thaliana* ppo gene, the primer comprising a SpeI restriction site (Example 1 II).

SEQ ID NO:9 Top strand primer for amplification of the *N. tabacum* psbA gene promoter, the primer comprising an EcoRI restriction site (Example 1 III).

SEQ ID NO:10 Bottom strand primer for amplification of the *N. tabacum* psbA gene promoter, the primer comprising a NcoI restriction site (Example 1 III).

SEQ ID NO:11 Top primer for amplification of the *A. thaliana* clpP gene promoter, the primer comprising an EcoRI restriction site (Example 1 V).

SEQ ID NO:12 Bottom primer for amplification of the *A. thaliana* clpP gene promoter, the primer comprising a BspHI restriction site (Example 1 V).

SEQ ID NO:13 Top primer for amplification of a new plastid DNA target locus, the primer comprising an XhoI restriction site (Example 4 I).

comprising an XhoI restriction site (Example 4 I).

SEQ ID NO:14 Bottom primer for amplification of a new plastid DNA target locus, the primer comprising an XbaI restriction site (Example 4 I).

SEQ ID NO:15 *Staphylococcus aureau* bacteriophage X2 promoter

SEQ ID NO:16 *Kluyvera* Bacteriophage kvp1 gen 10 5' UTR

SEQ ID NO:17 Bacteriophage T3 gene 9 3'UTR

SEQ ID NO:18 Nucleotide sequence of chimeric Staphylococcus bacteriophage X2 promoter-like sequence fused to the bacteriophage kvp1 gene 10 5' UTR.

SEQ ID NO:19 Nucleotide sequence of plastid transformation vector pEB10

SEQ ID NO:20 Top strand primer to amplify maize 16S NEP-PEP promoter (EcoRI site)

SEQ ID NO:21 Bottom strand primer to amplify maize 16S NEP-PEP promoter (XbaI site)

SEQ ID NO:22 Top strand primer to amplify bacteriophage T3 gene 5'UTR (RTK36)

SEQ ID NO:23 Bottom strand primer to amplify bacteriophage T3 gene 5'UTR (RTK39)

SEQ ID NO:24 Top strand primer to amplify maize 16S NEP-PEP (SmaI site) (RTK38)

SEQ ID NO:25 Bottom strand primer to amplify maize 16S NEP-PEP (BspHI site) (RTK37)

SEQ ID NO:26 Top strand of EcoRI-XbaI fragment of bacteriophage X2 promoter-like sequence SEQ ID NO:27 Bottom strand of EcoRI-XbaI fragment of bacteriophage X2 promoter-like sequence SEQ ID NO:28 Top strand primer for kpv1 gene 10 5'UTR SEQ ID NO:29 Bottom strand primer for kpv1 gene 10 5' UTR Definitions For clarity, certain terms used in the specification are defined and presented as follows:

"Associated with/operatively linked" refer to two nucleic acid sequences that are related physically or functionally. For example, a promoter or regulatory DNA sequence is said to be "associated with" a DNA sequence that codes for an RNA or a protein if the two sequences are operatively linked, or situated such that the regulator DNA sequence will affect the expression level of the coding or structural DNA sequence.

A "chimeric construct" or "chimeric gene" is a recombinant nucleic acid sequence in which a promoter or regulatory nucleic acid sequence is operatively linked to, or associated with, a nucleic acid sequence that codes for an mRNA or which is expressed as a protein, such that the regulatory nucleic acid sequence is able to regulate transcription or expression of the associated nucleic acid sequence. The regulatory nucleic acid sequence of the chimeric construct is not normally operatively linked to the associated nucleic acid sequence as found in nature.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

"Expression cassette" as used herein means a nucleic acid molecule capable of directing expression of a particular nucleotide sequence in an appropriate host cell or compartment of a host cell, comprising a promoter operatively linked to the nucleotide sequence of interest which is operatively linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular DNA sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue or organ or stage of development.

With respect to plastid transformation the expression cassette is designed in such a way that the promoter, the terminator and other regulatory sequences are functional within the plastids.

The term "gene" is used broadly to refer to any segment of DNA associated with a biological function. Thus, genes include coding sequences and/or the regulatory sequences required for their expression. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

The terms "heterologous" and "exogenous" when used herein to refer to a nucleic acid sequence (e.g. a DNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" nucleic acid (e.g. DNA) sequence is a nucleic acid (e.g. DNA) sequence naturally associated with a host cell into which it is introduced.

"homoplasmic" refers to plastids, plant cells and plants comprising only one single, uniform type of plastome copies, i.e. it refers to plastids which do not comprise different plastome copies or to plant cells or plants which do not comprise mixed plastid populations.

In the context of the present invention, an "isolated" DNA molecule or enzyme is a DNA molecule or enzyme that, by the hand of man, exists apart from its native environment and is therefore not a product of nature. An isolated DNA molecule or enzyme may exist in a purified form or may exist in a non-native environment such as, for example, in a transgenic host cell.

"Linked with" refers to a first nucleic acid sequence is linked with a second nucleic acid sequence when the sequences are so arranged that the first nucleic acid sequence affects the function of the second nucleic acid sequence. Preferably, the two sequences are part of a single contiguous nucleic acid molecule and more preferably are adjacent. For example, a promoter is operably linked to a nucleic acid encoding a protein if the promoter regulates or mediates transcription of the coding sequence in a cell. The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolised in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19: 5081 (1991); Ohtsuka et al., J. Biol. Chem. 260: 2605–2608 (1985); Rossolini et al., Mol. Cell. Probes 8: 91–98 (1994)). The terms "nucleic acid" or "nucleic acid sequence" may also be used interchangeably with gene, cDNA, and mRNA encoded by a gene.

"ORF" means open reading frame.

"Plastid lethal compound" refers to any compound affecting the viability of a wild-type plant cell plastid. Compounds affecting the viability of a wild-type plant cell plastid include, but are not limited to, compounds that rapidly degrade plastid membranes, inhibit plastid metabolic pathways (such as aromatic amino acid biosynthesis, photosynthesis, chlorophyll biosynthesis, ammonium assimilation, etc.), toxic compounds, proteases, nucleases, compounds that alter the pH of the cell, etc. Preferably, the plastid lethal compound degrades the inner and outer membranes of a wild-type plant cell plastid. Examples of such compounds include any herbicide, which includes but not limited to, glyphosate, butafenacil, phosphoinothricin, norfluorazone, atrizine, glufosinate, bromoxynil, and acifluorfen.

One skilled in the art will recognize that the ability of plastid lethal compounds to affect plastid viability is dependent upon the concentration of the compound in the medium, the length of time of exposure, and the plant tissue type and/or source.

"Plastid non-lethal compound" refers to compounds that affect the metabolism of the plant cell plastid and therefore slow or inhibit growth of the plastid or the cell as a whole but do not affect the viability of the plastid or the plant cell during the initial phase.

"Plastid transformation" refers to the genetic transformation of a plant cell or plant wherein foreign DNA sequences are delivered to the plastids and integrated into the plastid genome (plastome).

Two nucleic acids are "recombined" when sequences from each of the two nucleic acids are combined in a progeny nucleic acid. Two sequences are "directly recombined" when both of the nucleic acids are substrates for recombination. Two sequences are "indirectly recombined" when the sequences are recombined using an intermediate such as a cross-over oligonucleotide. For indirect recombination, no more than one of the sequences is an actual substrate for recombination, and in some cases, neither sequence is a substrate for recombination.

"Regulatory elements" refer to sequences involved in controlling the expression of a nucleotide sequence. Regulatory elements comprise a promoter operatively linked to the nucleotide sequence of interest and termination signals. They also typically encompass sequences required for proper translation of the nucleotide sequence.

"Transformation" is a process for introducing heterologous DNA into a plant cell, plant tissue, or plant. Transformed plant cells, plant tissue, or plants are understood to encompass not only the end product of a transformation process, but also transgenic progeny thereof.

"Transformed", "transgenic", and "recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

"transplastomic" refers to plastids, plant cells and plants comprising transformed plastomes.

DETAILED DESCRIPTION OF THE INVENTION

Section I: Plastid Transformation with Stable Integration of a Lethal Selectable Marker and A) Transient Integration or B) Unstable Integration of a Non-Lethal Selectable Marker A. Plastid Transformation with Stable Integration of a Lethal Selectable Marker and Transient Integration of a Non-Lethal Selectable Marker The present invention provides methods for producing transgenic plants having recombinant plastid genomes without the stable integration of an antibiotic resistance marker.

One aspect of the present invention provides plastid transformation vectors useful for obtaining transformed plastids. The vectors comprise a chimeric lethal selectable marker nucleic acid sequence encoding a protein that provides tolerance to a cell lethal compound and a chimeric non-lethal selectable marker nucleic acid sequence encoding a protein that provides resistance to a plastid non-lethal selective compound. In a vector according to the invention the lethal selectable marker nucleic acid sequence is flanked by plastid targeting sequences whereas the non-lethal selectable marker nucleic acid sequence is located in the backbone of the vector outside of the plastid targeting sequences.

The chimeric lethal selectable marker nucleic acid sequence preferably comprises a promoter sequence functional in the plastid, a regulatory 5'-untranslated region (5'UTR), a DNA sequence encoding a protein conferring tolerance to a cell lethal compound and a 3'-untranslated region (3'UTR).

The chimeric non-lethal selectable marker nucleic acid sequence preferably comprises a promoter sequence functional in the plastid, a regulatory 5'UTR, a DNA sequence encoding a non-lethal selectable marker encoding a protein conferring resistance to a plastid non-lethal compound, and a 3'UTR.

Another aspect of the present invention provides plastid transformation vectors useful for obtaining transformed plastids and integrating DNA sequences into the plastid genome. Such DNA sequences can, for example, be genes, chimeric nucleic acid sequences or molecules, or expression cassettes for expression of a gene product or gene products within the transformed plastids. These plastid transformation vectors contain in addition to the previously described features at least one such DNA sequence that is linked to the chimeric lethal selectable marker nucleic acid sequence within plastid targeting sequences. An expressible DNA sequence typically comprises a promoter sequence functional in the plastid, a regulatory 5'UTR, at least one DNA segment encoding a gene product of interest and a 3'UTR. Alternatively, the DNA sequence encoding one or several gene products and the chimeric lethal selectable marker can be expressed from a single promoter in an operon-like polycistronic gene.

Numerous methods known to those skilled in the art are used in making the constructs and vectors of the present invention such as, but not limited to, ligation, restriction enzyme digests, polymerase chain reaction (PCR), in vitro mutagenesis, linkers and adapters additions, etc, and are described for example, in Sambrook et al., *Molecular Cloning: a laboratory manual*, $2^{nd}$ ed. (1989). Therefore, nucleotide transitions, transversions, insertions, deletions may be performed on nucleic acid molecules that are employed in the regulatory regions, the nucleic acid sequences of interest for expression in the plastids.

The present invention also provides methods for transforming plastids using a two-step selection protocol with plastid non-lethal compounds and cell lethal compounds. Initial plastid transformants are selected on a medium containing a plastid non-lethal compound. The selection is facilitated by the expression of a transiently integrated non-lethal selectable marker gene in the plastid genome. Once a sufficient number of transformed plastids per cell has accumulated, the non-lethal compound medium is replaced by a medium containing a cell lethal compound that selects for plastid genomes expressing the protein that confers tolerance to this compound.

Alternatively, initial transformants are selected on a medium containing both, a plastid non-lethal compound and a cell lethal compound. Once a sufficient number of transformed plastids per cell accumulated, the selection is continued on medium containing the cell lethal compound only.

In a preferred embodiment of the invention the plastid non-lethal compound is an antibiotic and the non-lethal marker is an antibiotic resistance gene.

In another preferred embodiment the cell lethal compound is a herbicide, preferentially a herbicide from the group of PPO inhibitors.

Plastid Transformation with Stable Integration of ppo and Transient Integration of aadA In a preferred embodiment of the present invention the lethal selectable marker gene is a protoporphyrinogen oxidase (ppo) conferring tolerance to the cell lethal compound butafenacil, and the non-lethal selectable marker gene is aminoglycoside adenyltransferase (aadA) conferring resistance to the plastid non-lethal compound spectinomycin.

The present invention provides a method for producing a transgenic plant having recombinant plastid genomes without stable integration of an antibiotic selectable marker such as aadA. Initial plastid transformants are selected on spectinomycin containing medium based on the expression of the aadA gene which is transiently integrated into the plastid genome. Once a sufficient number of transformed plastids per cell has accumulated, tolerance to butafenacil is conferred to the cell by the expression of the ppo gene which is stably integrated into the plastome. The removal of the antibiotic resistant gene and the segregation and selection of homoplasmic transformants is achieved by switching from spectinomycin to butafenacil selection.

B. Plastid Transformation with Stable Integration of a Lethal Selectable Marker and Unstable Integration of a Non-Lethal Selectable Marker The present invention provides a method to stably integrate a transgene or transgenes of interest into the plastid genome by targeting it into a non-essential plastid genome region wherein the selectable marker is unstably inserted into the plastid genome by targeting it to the plastid genome in such a way that it disrupts an essential plastid gene. This invention is based on the fact that targeted disruption of essential plastid genes is unstable because the disrupted genes revert to their wild-type conformation when the selective pressure is removed Plastid genomes possess several genes (such as ycf1, ycf2 and clpP) that are essential for cell survival. Previous attempts to inactivate such genes by targeted disruption with selectable marker genes (Shikanai et al., Plant Cell Physiol. 42:264–73, 2001; Drescher et al., Plant J. 22:97–104, 2000; Boudreau et al., Mol. Gen. Genet. 253:649–53, 1997; Huang et al., Mol. Gen. Genet. 244: 151–9, 1994) could only produce heteroplasmic populations of plastid comprising both, the disrupted and wild-type genes. The insertion of the selectable marker into these genes is unstable and removal of the selective pressure results in the loss of the selective marker and in the reversion to homoplasmic plastid populations having only wild-type copies of the essential gene (Drescher et al., Plant J.22: 97–104, 2000; Fischer et al., Mol. Gen. Genet. 251:373–80, 1996).

One aspect of the present invention provides plastid transformation vectors useful for obtaining transformed plastids. The plastid transformation vector comprises a DNA segment homologous to a plastid locus containing at least a part of an essential plastid gene sequence and an adjacent non-essential plastid sequence, such as an intergenic region. The vectors comprise a chimeric non-lethal selectable marker gene, encoding a protein which provides resistance to a plastid non-lethal compound, wherein the non-lethal selectable marker gene is inserted into the essential plastid gene sequence. The vector further comprises a chimeric lethal selectable marker gene, encoding a protein that provides tolerance to a cell lethal compound, wherein the lethal selectable marker gene is inserted into the non-essential sequence plastid sequence. The chimeric lethal selectable marker gene comprises a promoter sequence functional in the plastid, a regulatory 5'UTR, a DNA sequence encoding a protein conferring tolerance to a cell lethal compound, and a plastidic 3'UTR.

The chimeric non-lethal selectable marker gene comprises a promoter sequence functional in the plastid, a regulatory 5'UTR, a DNA sequence encoding a protein conferring resistance to a plastid non-lethal compound, and a 3'UTR. Both, lethal and non-lethal selectable marker cassettes are flanked by plastid DNA sequence for targeted insertion in the plastid genome by homologous recombination. The plastid DNA sequence linking the genes to be inserted need to be sufficiently long to allow both, linked and unlinked recombination of the genes with the plastid genome. Preferentially, such linking plastid DNA sequences are at least 200 bp long.

Another aspect of the present invention provides plastid transformation vectors useful for obtaining transformed plastids and for expressing a gene product or gene products within the transformed plastids. The plastid transformation vectors comprise in addition to the previously described plastid targeting segments with selectable marker genes at least one expressible DNA sequence that is linked to the chimeric lethal selectable marker gene in the non-essential sequence. The expressible DNA sequence comprises a promoter sequence functional in the plastid, a regulatory 5'UTR, a DNA segment encoding a gene product and a plastidic 3'UTR.

Alternatively, the DNA sequence encoding one or several gene products and the chimeric lethal selectable marker are expressed from a single promoter in an operon-like polycistronic gene.

The present invention also provides methods for transforming plastids using a two-step selection protocol with plastid non-lethal and cell lethal compounds. Initial plastid transformants are selected on a medium containing a plastid non-lethal compound. The selection is facilitated by the expression of a non-lethal selectable marker gene integrated in the targeted plastid essential gene. Once a sufficient number of transformed plastids per cell has accumulated, the non-lethal compound medium is replaced by a medium containing a cell lethal compound that selects for plastid genomes expressing the protein that confers tolerance to this compound. After several rounds of tissue subculture on lethal selective media the plastid genomes are rendered homoplasmic for the lethal selectable marker gene or the lethal selectable marker with expressible DNA sequence(s), and wild-type for the targeted essential gene.

Alternatively, initial transformants are selected on a medium containing both, a plastid non-lethal compound and a cell lethal compound. Once a sufficient number of transformed plastids per cell has accumulated, the selection is continued on medium containing a cell lethal compound only.

Plastid Transformation with Stable Integration of ppo and Unstable Integration of aadA In a preferred embodiment of the present invention the lethal selectable marker gene is protoporphyrinogen oxidase (ppo) conferring tolerance to the cell lethal compound butafenacil, and the non-lethal selectable marker gene is aminoglycoside adenyltransferase (aadA) conferring resistance to the plastid non-lethal compound spectinomycin. The present invention provides a method for producing a transgenic plant having recombinant plastid genomes without stable integration of an antibiotic selectable marker such as aadA. Initial plastid transformants are selected on spectinomycin containing medium based on the expression of the aadA gene which is unstably integrated into the plastid genome, disrupting an essential plastid gene. Once a sufficient number of transformed plastids per cell has accumulated, tolerance to butafenacil is conferred to the cell by the expression of the ppo gene which is stably integrated into the plastome. The reversion of the disrupted essential plastid gene to the wild-type gene and the segregation and selection of homoplasmic transformants is achieved by switching from spectinomycin to butafenacil selection.

Section II: Methods for Selecting Homoplasmic Transplastomic Plants Expressing the ppo Gene in their Plastids The invention relates to methods for selecting homoplasmic plant cells or plants comprising transplastomic plastids having the ppo gene integrated into their plastome with the exclusion of any antibiotic resistance gene.

These methods employ a ppo plastid expression cassette, which is flanked by a sequence homologous to plastid DNA, an aadA plastid expression cassette, which is apart from the flanking sequence of the ppo cassette, and either one of the two phase selection strategies provided by the invention, comprising using the ppo gene as selectable marker gene during the segregation phase of heteroplasmic plastid populations and the selection of homoplasmic plant cells to obtain transplastomic plants having the ppo gene integrated into their plastome with the exclusion of the antibiotic resistance gene aadA.

A further aspect of the invention relates to the extension of plastid transformation methods to non pigmented plant material. The invention provides selection strategies comprising using a lethal selectable marker gene for plastid transformation and a cell lethal compound such as Formula XVII as selective agent, wherein green pigmentation is not essential for the selected transplastomic phenotype. These selection strategies therefore have the potential to be applied to green tissue as well as to non-green tissue for plastid transformation.

The lethal selectable marker gene ppo and the antibiotic resistance gene aadA are co-delivered into the transformation targets in the same or in separate constructs, wherein the ppo cassette comprises its own flanking sequence which is homologous to a plastid DNA fragment, while the aadA cassette is apart from the flanking sequence of the ppo cassette. The ppo cassette comprises a 5'-promoter, the ppo gene, and a 3'UTR, designed for expression in the plastid, while the aadA cassette comprises a 5'-promoter, the aadA gene and a 3'UTR, designed for expression in the plastid.

The selection procedure consists of two phases. During the first selection phase, cells containing transplastomic plastids are selected on medium comprising the non-lethal selective compound spectinomycin or streptomycin. Alternatively, the selection medium used during the first selection phase comprises spectinomycin or streptomycin in combination with the herbicide Formula XVII as a cell-lethal selective agent.

The selection of the first phase on medium containing the non-lethal compound is carried out for a period of time in which resistant events are not yet visually detectable. A person skilled in the art will know how to determine this time period, e.g. based on tissue culture parameters which are specific for the plant species to be transformed. The first selection phase lasts for about five days to about eight weeks, more specifically for about one week to about six weeks. Preferentially, the first selection phase is about two to four weeks.

Alternatively, the first selection phase can be extended until resistant events become visually detectable. Depending on the plant species to be transformed and the type of explant used resistant events become visible after about one week to about fifteen weeks, more specifically after about three weeks to about ten weeks. When the first selection phase is extended until resistant events are visually detectable, the first selection phase typically lasts for about five weeks.

The second selection phase which follows the initial selection on spectinomycin is carried out on medium containing the cell-lethal agent Formula XVII as selective agent. The segregation and selection process during this phase results in the rapid loss of the antibiotic resistant gene aadA and the establishment of a homoplasmic plastid population having the ppo gene stably integrated into the plastome. The thus obtained transplastomic cells are then regenerated into homoplasmic plants which express the ppo gene in their plastids and which transmit the transplastomic plastids to their progenyThe homoplasmic PPO transplastome plants result in much higher herbicide tolerance than nuclear transformed plants with the same gene. Furthermore, much higher herbicide resistance is obtained with homoplasmic transplastomic expressing the ppo gene in their plastids plants than with nuclear transformants expressing ppo in the nucleus.

Any method know for transforming plant cell plastids available may be employed in the present invention that result in plant cells containing a population of plastids into which have been introduced a recombinant nucleic acid construct having a DNA sequence encoding for a protein that provides tolerance to a plastid lethal compound or a plastid non-lethal compound as the case may be. Plastid transformation methods include, but are not limited to, particle bombardment, PEG mediated transformation, Stable transformation of tobacco plastid genomes by particle bombardment has been reported (Svab et al. (1990) Proc. Natl. Acad. Sci. USA 87:8526–8530; Svab and Maliga (1993) Proc. Natl. Acad. Sci. USA 90:913–917) and PEG mediated transformation of plastids is described by Koffer et al. (1998) in Vitro Cell. Biol.-Plant, 34:303–309 Other methods for introducing recombinant constructs into plant cell plastids are known in the art, and are described for example in Svab et al. (1990) Proc Natl. Acad. Sci. USA 87:8526–8530, Sikdar et al. (1998) Plant Cell Reports 18:20–24, PCT Publication WO 97/2977, and Sidorov et al. (1999) Plant J. 19(2):209–216. Additional methods for introducing two constructs into a plant cell plastid are described for example in Carrer et al. Biotechnology 13:791–794 (1995). The methods described in the above references may be employed to obtain plant cells transformed with the plastid transformation constructs described herein.

The regeneration of whole plants from a transformed cell contained in the tissue used in transformation involves several growth stages. Typically, a tissue, having been excised from an adult plant or germinated seedling, is placed on a chemically defined medium under sterile conditions. By growing the explant under such controlled conditions for a period of time, an undifferentiated mass of cells, referred to as a callus, may form. By culturing this callus under the proper set of conditions, e.g., nutrients, light, temperature, humidity, and by providing the proper combination and concentration of plant growth regulators, the calli may be induced to form differentiated cells and regenerate plant shoots. Plant shoots, sometimes referred to as plantlets, containing meristem tissue are then transferred to a media for the induction of root production.

The selective media used and described herein may be liquid or solid, such as by the addition of a solidifying agent, such as agar. Liquid selective media allows for greater surface area of contact of the plant tissue with the selective media containing particular hormones, particular selective agents and other substances necessary to obtain regeneration.

The above disclosed embodiments are illustrative. This disclosure of the invention will place one skilled in the art in possession of many variations of the invention. All such obvious and foreseeable variations are intended to be encompassed by the appended claims.

EXAMPLES

Example 1

Preparation of the Plastid Transformation Vector for Transient Integration of aadA I. Amplification of the Maize Plastid 16S PEP-NEP rRNA Gene Promoter Fused to the *N. tabacum* Plastid rbcL Ribosome Binding Site (RBS)

The Maize 16S PEP-NEP rRNA gene promoter (*Zea mays* complete chloroplast genome, accession number X86563, position 94966 to 95115) was isolated by PCR amplification from Maize 6N615 DNA using a top strand primer comprising an introduced EcoRI restriction site at the 5'end of the 16S rRNA gene promoter region (SEQ ID NO: 5; 5'-GCCA GAATTCACCACGATCGAACGGGAATGGATA-3', EcoRI site is underlined) and a bottom strand primer that extends to the 16 S rRNA gene promoter, mutates one ATG downstream of the transcription start site by changing position (T to G), fuses the tobacco rbcL RBS (*N. tabacum* complete chloroplast genome, accession number NC_001879 position 577569 to 57585) as a 5'-extension to the 3'-end of the 16S rRNA gene 5'UTR and introduces a BspHI site at the 5'-end of the RBS (SEQ ID NO: 6; 5'-GCCG TCATGAATCCCTCCCTACAACTGATTCGGAATTGT-CTTTCCTTCCAAGGATA ACTFGTATCCAGGCGCT-TCAG-3', BspHI restriction site is underlined). PCR amplification was performed with the Pfu Turbo DNA polymerase kit (Stratagene, LaJolla Calif.) in a Perkin Elmer Thermal Cycler 480 according to the manufacturer's recommendations (Perkin Elmer/Roche, Branchburg. N.J.) as follows: 5 min 95° C., followed by 5 cycles of 1 min 95° C./2 min 49° C./1 min 72° C., then 25 cycles of 1 min 95° C./2 min 55° C./1 min 72° C.

The DNA sequence of the maize plastid 16S PEP-NEP rRNA gene promoter fused to the *N. tabacum* plastid rbcL ribosome binding site (RBS) is provided in SEQ ID NO:4. In the representation of SEQ ID NO:4 below the 16S rRNA gene promoter sequence is underlined; the mutated nucleotide is in bold; the initiation codon (ATG) is in small caps:

```
  1 GAATTCACCA CGATCGAACG GGAATGGATA AGAGGCTTGT GGGATTGACG

50 TGATAGGGTA GGGTTGGCTA TACTGCTGGT GGCGAACTCC AGGCTAATAA

100 TCTGAAGCGC CTGGATACAA GTTATCCTTG GAAGGAAAGA CAATTCCGAA

150 TCAGTTGTAG GGAGGGATTC atg
```

II. Construction of a Maize 16S rRNA Promoter Fused to the *N. tabacum* rbcL Gene Ribosome Binding Site (RBS), the *Arabidopsis thaliana* ppo Gene and *N. tabacum* Plastid rps16 3'UTR Cassette for Plastid Selection.

The chimeric *A. thaliana* ppo gene was created through the following cloning steps. The plasmid pAT259 containing the Arabidopsis ppo coding sequence was created by ligating a 450 bp EcoRI-SfuI comprising part of the Arabidopsis ppo gene which contains the pAraC-2Met and pAra305 Leu point mutations (described in U.S. Pat. No. 6,084,155) to a 4.1 kb EcoRI-SfuI fragment from pPH141 (also described in U.S. Pat. No. 6,084,155). A SpeI restriction site was added at the 3' end of ppo gene by PCR amplification using pAT259 as DNA template and the following top strand primer (SEQ ID NO: 7; 5'-CCACGCACGCAAGGAGT-TGA-3') and the bottom strand primer (SEQ ID NO: 8; 5'-CGGTACTAGTCTGGGAGATTTAATGTT-3', SpeI restriction site is underlined).

The plasmid pAT260 was formed by ligating the 2.8 bp NcoI-SpeI digested pLITMUS28 vector with a 1.1 kb NcoI-EcoRI fragment from pAT259 containing the 5'-end of the ppo coding sequence and a 337 bp EcoRI-SpeI PCR amplified fragment containing the 3'-end of the ppo gene.

Plasmid pAT263 was obtained by ligating a 1.5 kb NcoI-SpeI fragment from pAT260 comprising the *Arabidopsis* ppo coding sequence with a 2.8 kb EcoRI-SpeI fragment from pAT229 (described in WO 00/20612) comprising the tobacco plastid rps16 3'UTR integrated into the pUC19 vector (New England Biolabs) and the 145 bp EcoRI-NcoI Maize 16SrRNA PEP-NEP-rbcL (RBS) PCR amplified promoter sequence.

III. Amplification and Cloning of the *N. tabacum* Plastid psbA Promoter.

The tobacco psbA gene promoter (*N. tabacum* complete chloroplast genome, accession number NC_001879, position 1596 to 1745) was isolated by PCR amplification of DNA isolated from the *N. tabacum* cv. 'Xanthi' using a top strand primer comprising an introduced EcoRI restriction site at the 5'-end of the psbA gene promoter region (SEQ ID NO: 9; 5'-TTAAGAATTCGAATAGATCTACATA-3', EcoRI site is underlined) and a bottom strand primer comprising an introduced NcoI site at the end of psbA 5'UTR (SEQ ID NO: 10; 5'-CAGCCATGGTAAAATCTTGGTT-3', NcoI restriction site is underlined). PCR amplification was performed with the Pfu Turbo DNA polymerase kit (Stratagene, LaJolla Calif.) in a Perkin Elmer Thermal Cycler 480 according to the manufacturer's recommendations (Perkin Elmer/Roche, Branchburg, N.J.) as follows: 1 min 94° C., followed by 35 cycles of 1 min 94° C./1 min 45° C./1 min 72° C., then 10 min 72° C. The predicted 16 bp amplification product was digested with EcoRI and NcoI and ligated in the respective sites of pLITMUS28 (New England Biolabs, Beverly Mass.) to form the pPB30 plasmid.

IV. Preparation of the Chimeric Gene containing *N. tabacum* psbA Promoter Fused to aadA.

Plasmid pPB37 comprising the tobacco psbA promoter upstream of the aadA coding sequence, a bacterial gene encoding the enzyme aminoglycoside adenyltransferase that confers resistance to spectinomycin and streptomycin, was obtained by ligating the 2.8 kb EcoRI-SpeI digested pLitmus28 vector with the 149 bp EcoRI-NcoI tobacco psbA promoter fragment from pPB30 and a 813 bp BspHI-SpeI fragment from pAT229 which contains the aadA coding sequence.

V. Construction of a Chimeric Gene Containing the *Arabidobsis thialiana* clpP Promoter Fused to a Gus Reporter Gene and the *A. thaliana* Plastid psbA 3'UTR.

Plasmid pAT242 comprising a gus chimeric gene was obtained by the following cloning strategy. The *A. thaliana* clpP promoter was PCR amplified from plasmid pPH146b (described in U.S. Pat. No. 6,362,398) using a top strand primer comprising an introduced EcoRI restriction site at the 5'-end of the clpP gene promoter region (SEQ ID NO: 11; 5'-GCG<u>GAATTC</u>ATCATTCAGAAGCCCGTTCGT-3', EcoRI site is underlined) and a bottom strand primer comprising an introduced BspHI site at the 5'-end of clpP 5'UTR (SEQ ID NO:12; 5'-GCG<u>TCATGA</u>AATGAAAGAAAAAGAGAAT-3', BspHI restriction site is underlined). PCR amplification of the 250 bp fragment was performed with the Pfu Turbo DNA polymerase kit (Stratagene, LaJolla Calif.) in a Perkin Elmer Thermal Cycler 480 according to the manufacturer's recommendations (Perkin Elmer/Roche, Branchburg. N.J.) as follows: 1 min 94° C., followed by 35 cycles of 1 min 94° C./1 min 45° C./1 min 72° C., then 10 min 72° C. pAT242 was created by ligating the 238 bp EcoRI-BspHI fragment from the *A. thaliana* clpP promoter PCR amplification to a 2.1 kb NcoI-HindIII fragment from pAT221 containing the gus gene linked to the *A. thaliana* plastid psbA 3'UTR (described in WO 00/20612) and to the 3.2 kb HindIII-EcoRI digested pUC21 vector.

VI. Insertion of the ppo and aadA Chimeric Genes in a Tobacco Plastid Transformation Vector.

Plasmid pPB2 having the chimeric ppo and gus genes cloned in opposite orientation was created by ligating a 1.8 kb HindIII-EcoRI fragment from pAT263, which was fully cut with HindIII but only partially cut with EcoRI, containing the Maize 16S rRNA PEP-NEP-rbcL(RBS)::ppo::*N. tabacum* rps16 3'UTR chimeric gene, a 2.3 kb EcoRI-PstI fragment containing the chimeric *A. thaliana* clpP promoter::gus::*A.thaliana* psbA 3'UTR gene from plasmid pAT242 and the 2.9 kb HindIII-PstI digested bluescript SK+vector (Stratagene, LaJolla Calif.). The pPB6 plastid transformation vector was made by flanking the chimeric ppo and gus genes with tobacco chloroplast sequence. A 4.1 kb PstI fragment comprising both chimeric genes from pPB2 was ligated to the PstI linearized pAT218 plasmid (PCT WO 00/20612) containing the plastid targeting sequence. The plastid transformation vector pPB97 was made by replacing the pPB6 gus coding sequence with the *A. thaliana* clpP promoter by the *N. tabacum* psbA promoter::aadA gene cassette from plasmid pPB37. A 962 bp EcoRI-SpeI fragment from a fully EcoRI but partially SpeI digested pPB37 plasmid was ligated to a 6.7 kb EcoRI-XbaI fragment from a fully XbaI but partially EcoRI digested pPB6 plasmid.

II. Creation of the Plastid pEBPPOt Transformation Vector.

The plastid transformation vector pEBPPOt (SEQ ID NO: 1) for stable integration of the *A. thaliana* ppo gene into the plastid genome but only transient insertion of the aadA gene was created using the following strategy. The *N. tabacum* psbA promoter::aadi::*A. thaliana* psbA 3'UTR chimeric gene was removed from pPB97 by partially digesting the plasmid with EcoRI and fully cutting it with HindIII. Following the restriction digestions the ends of the resulting fragments were rendered blunt with the T4 DNA polymerase. A 6.5 kb fragment comprising the vector with the chimeric ppo gene, the plastid targeting sequence and a 1.2 kb fragment containing the aadA chimeric gene was isolated. The 6.5 kb vector fragment was self ligated to yield pEBPPO. This plasmid was subsequently linearized with NgomIV, rendered blunt with T4 DNA polymerase and ligated to the 1.2 blunt aadA fragment to yield pEBPPOt. Plasmids having the chimeric aadA gene in either orientation was obtained but only the one having aadA oriented towards the bla gene of the vector was retained (FIG. 1).

Example 2

Figure 2:
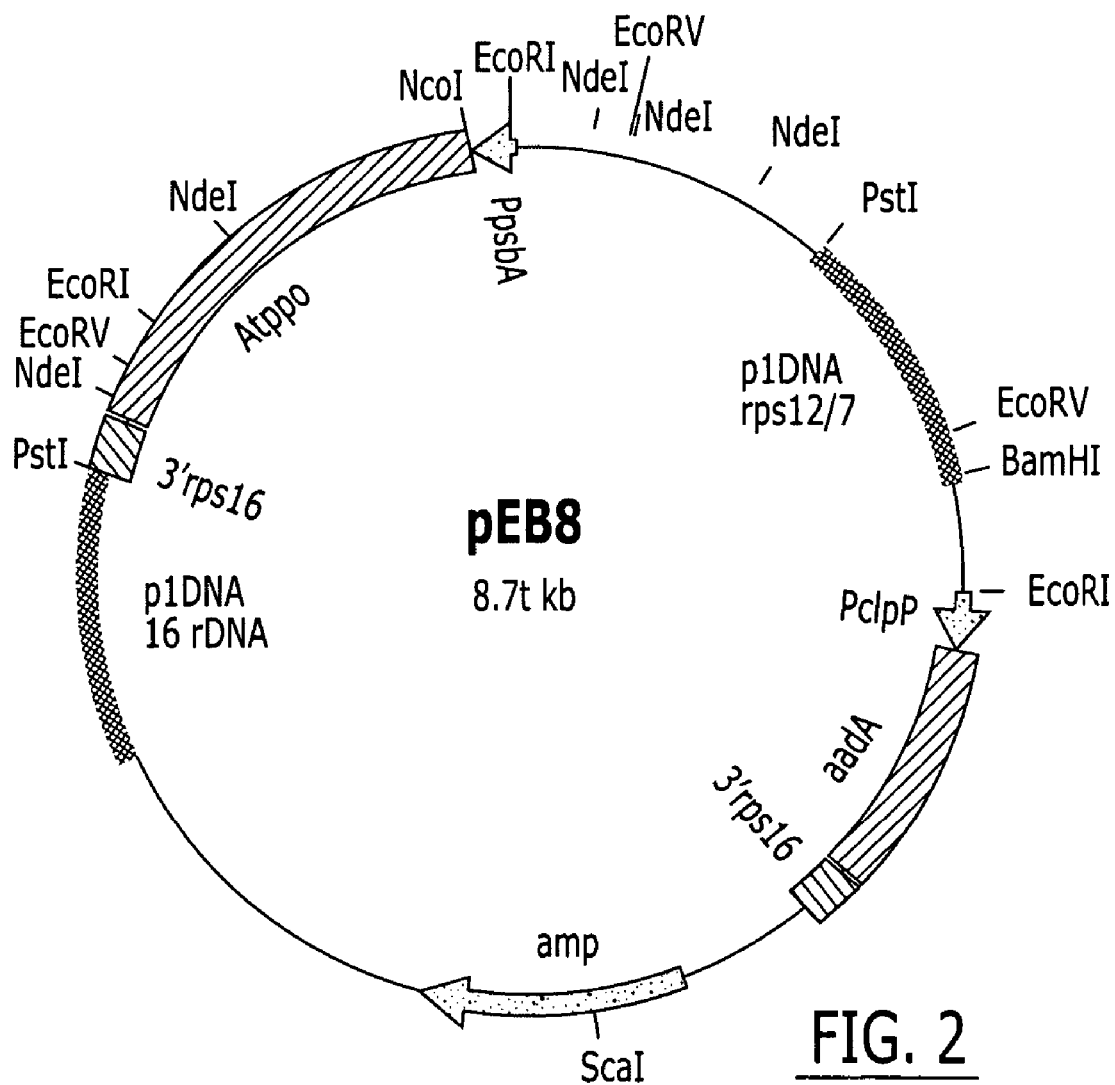
FIG. 2. Map of the pEB8 plastid transformation vector (SEQ ID NO:2). Plastid targeting sequence plDNA 16rDNA and rps12/7 are represented by hatched lines. Components of the chimeric *A. thaliana* ppo gene are *N. tabacum* psbA promoter (PpsbA), the *A. thaliana* ppo gene (Atppo) and the *N. tabacum* plastid rps16 3'UTR (3'rps16). Components of the chimeric aadA gene are the *N. tabacum* clpP plastid promoter (PclpP), the aadA coding sequence (aadA) and the *N. tabacum* plastid rps16 3'UTR (3'rps16). The ampicilline resistance gene on the vector backbone sequence (amp) is encoded by the bla gene and indicated by an arrow. The restriction sites are marked for: PstI, NdeI, EcoRI, EcoRV, BamHI and ScaI.

Preparation of a Plastid Transformation Vector for Stable Integration of Exogeneous DNA Linked to the Chimeric ppo Gene Under the Control of the Plastid Maize16S Pep-Nep rRNA Gene Promoter and Transient Integration of a Chimeric aadA Gene Under the Control of the N. tabacum clpP Promoter The plasmid pPB96 was obtained by a four way ligation of the 149 bp EcoRI-NcoI N. tabacum plastid psbA promoter from pPB30, a 1.5 kb NcoI-SpeI fragment from pAT260 containing the A. thaliana ppo coding sequence, a 4.0 kb BamHI-SpeI fragment from pPB67b containing the N. tabacum plastid rps16 3'UTR linked to the N. tabacum 16S rDNA portion of the plastid targeting sequence and the pBluescript SK+vector, and a 1.9 kb EcoRI-BamHI fragment from pPB67b which contains a portion of the rps7/12 plastid targeting sequence. The plastid transformation vector pEB8 was obtained by ligating a NgomIV linearized blunt ended pPB96 plasmid with a 1.2 blunt fragment containing a N. tabacum clpP plastid promoter (described in U.S. Pat. No. 6,084,155) fused to the aadA gene and the N. tabacum plastid rps16 3'UTR chimeric gene yielding plasmid pEB8a and pEB8b, which differ only in the orientation of the chimeric aadA gene in the plasmid. Only pEB8a (SEQ ID NO:2, FIG. 2) having aadA directed towards the bla gene of the vector was retained for plastid transformation.

Example 3

Biolistic Transformation of the Tobacco Plastid Genome with the Plastid Transformation Vectors pEBPPOt and pEB8 and Selection (see Example 6 for a Detailed Description of the Transformation and Selection Methods)

After delivery of pEBPPOt (FIG. 1, SEQ ID NO:1) or pEB8 (FIG. 2, SEQ ID NO:2) into the plastid the entire vector integrates into the plastid genome in a first recombination event. Initial plastid transformants are selected by spectinomycin due to the expression of the aadA gene transiently integrated into the plastid genome. Since the cpDNA sequences flanking the ppo gene in the vector provide two different cross-over loci, the recombination between the plastid genome and the vector results in a mixed population of transformed genomes having the inserted vector in different conformation (A and B). Switching to butafenacil selection favors the stable insertion of the ppo gene and the excision of the aadA gene together with the vector backbone sequence. The loss of the vector sequence is mediated by an intra-recombination event between direct repeated DNA sequences that were created when the vector inserted into the genome. Further the segregation of the plastid population under butafenacil selection results in the enrichment of ppo transformed plastid genomes without the aadA marker and will finally lead to homoplasmic cells.

PCR analysis of DNA samples from selected pEBPPOt and pEB8 events obtained from initial spectinomycin selection showed that both, the aadA and the ppo gene, are present in the transformants. Subsequently, after two to three rounds of subculture on butafenacil containing medium, PCR analysis of DNA samples from same events confirmed the loss of the aadA gene while the ppo gene is retained in the transformants.

Southern blot analysis was used to demonstrate that the ppo gene could be inserted in the plastid genome to homoplasmicity upon butafenacil selection. Total cellular DNA from ten pEBPPOt transformants that were subjected to three or four subculture rounds on butafenacil selective conditions was analyzed by Southern blot hybridization. DNA of the wild-type and of transformants was digested with BamHI and hybridized with a chloroplast DNA (cp-DNA) specific probe. This probe hybridized with a 3.3 kb fragment of wild-type DNA, whereas it predominately hybridized with a 5.1 kb DNA fragment in eight of the transformants indicating that the 1.8 kb ppo gene is inserted to homoplasmicity in most of these events. In lines 4 and 9 both fragments are detectable, indicating the occurrence of a heteroplasmic (mixed) population of wild-type and ppo transformed plastid genomes. Four different plastid genome populations are observed in these lines: a wild-type genome (3.3 kb), a ppo transformed genome (5.1 kb) and vector inserted genomes in two different conformations (vector insertion A and B, 7.6 and 5.8 kb, respectively). Reprobing the BamHI Southern blot with an aadA specific probe, confirmed that the homoplasmic transformants add lost the antibiotic marker and that the vector was inserted in different conformation (7.6 and 5.8 kb BamHI fragments) in the plastid genomes of the heteroplasmic lines 4 and 9. A Southern blot of SpeI digested DNA samples probed with the same aadA probe also showed that only the heteroplasmic lines 4 and 9 have the antibiotic marker (0.9 kb) whereas the other transformants have lost it.

Southern hybridization analysis of BamHI digested DNA for the identification of homoplasmic pEBPPOt plastid transformants.

Southern blot analysis was used to demonstrate that exogenous DNA linked to the ppo gene from pEB8 vector could be inserted in the plastid genome to homoplasmicity upon butafenacil selection. Total cellular DNA from two pEB8 transformants that were subjected to four subculture rounds on butafenacil selective conditions was analyzed by Southern blot hybridization. DNA of the wild-type and of transformants was digested with BamHI and hybridized with a chloroplast DNA (cpDNA) specific probe. This probe hybridized with a 3.3 kb fragment of wild-type DNA, whereas it predominately hybridized with a 6.1 kb DNA fragment the transformants indicating that the 2.8 kb sequence containing the exogenous DNA linked to the ppo gene is inserted to homoplasmicity in these events.

Example 4

Preparation of the Plastid Transformation Vector for Unstable Integration of aadA I. Cloning of a New Plastid Target Locus A 4.7 kb fragment of tobacco plastid DNA (N. tabacum complete chloroplast genome, accession number NC_001879, position 93132 to 97844 and 144782 to 149494) was isolated by PCR amplification of DNA isolated from the N. tabacum cv. 'Xanthi' using a top strand primer comprising an introduced XhoI restriction site (SEQ ID NO: 13; 5'-AGTTAT CTCGAGTGAGAGAAAGAAGTGAGGAAT-3', XhoI site is underlined) and a bottom strand primer comprising an XbaI site (SEQ ID NO: 14; 5'-TTC TCTAGAAGAAATACGGGG-3', XbaI restriction site is underlined). PCR amplification was performed with the Pfu Turbo DNA polymerase kit (Stratagene, LaJolla Calif.) in a Perkin Elmer Thermal Cycler 480 according to the manufacturer's recommendations (Perkin Elmer/Roche, Branchburg. N.J.) as follows: 1 cycle at 95° C. for 5 min where enzyme was added 2 min before the end of the cycle, followed by 30 cycles of 1 min 94° C./1 min 45° C./4 min 72° C., then 1 cycle for 10 min at 72° C. The predicted 4.7 kb amplification product was digested with XhoI and XbaI and ligated in the respective sites of pLITMUS28 (New England Biolabs, Beverly Mass.) to form the pEBNY2 plasmid.

II. Construction of Novel Plastid Transformation Vector

The plasmid pEBNY2 was linearized with PstI restriction endonuclease. The chimeric aadA gene was removed from pPB97 by partially digesting the plasmid with EcoRI and fully cutting it with HindIII. Following the restriction digestions the ends the 7.5 kb PstI linearized pEBNY2 plasmid and of the 1.2 kb HindIII-EcoRI fragment containing the aadA chimeric gene were rendered blunt with the T4 DNA polymerase. Subsequently, these fragments were ligated together to yield the plasmid pEBNY2+aadA. Plasmids having the chimeric aadA gene in either orientation were obtained but only the one having aadA oriented in opposite direction of the ycf2 gene was retained.

Figure 3:
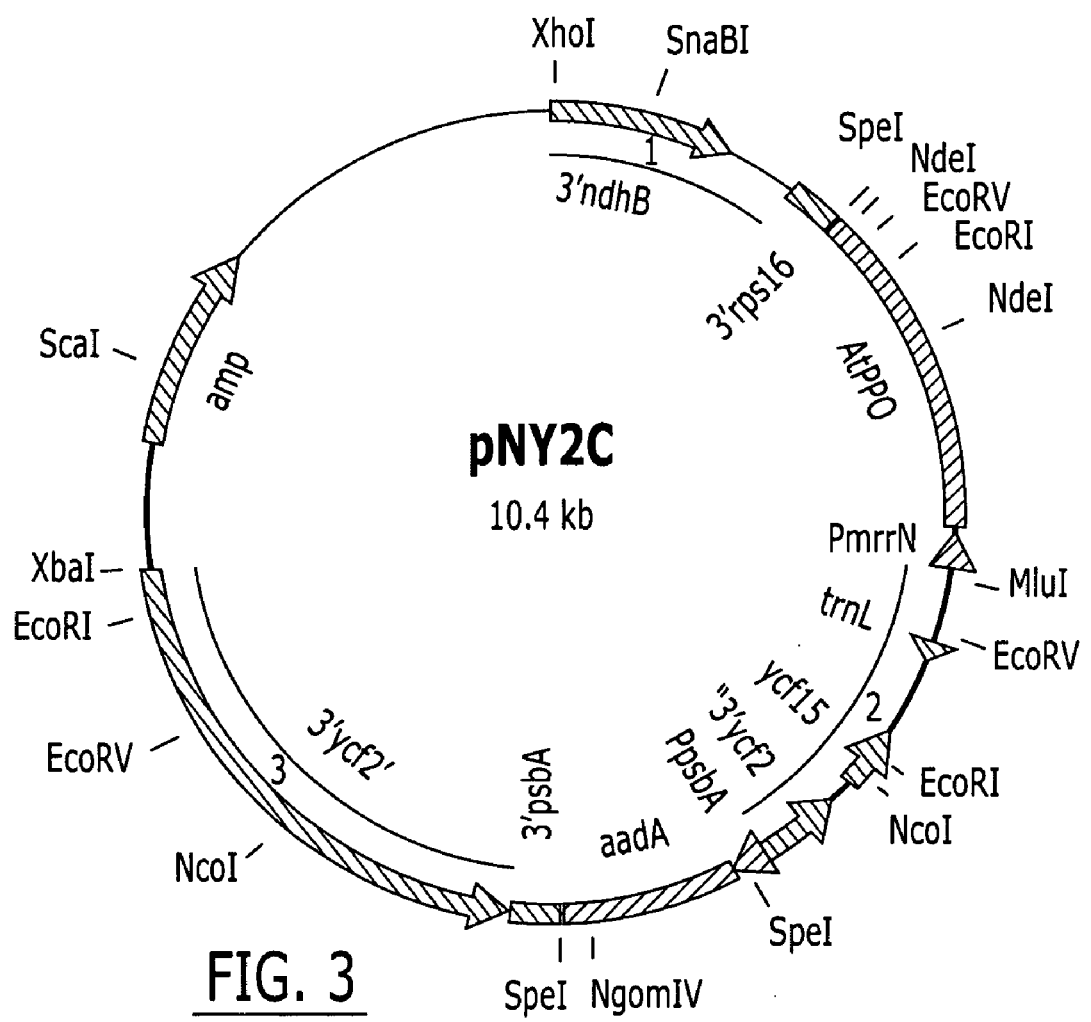
FIG. 3. Map of the pNY2C plastid transformation vector (SEQ ID NO:3). The plastid targeting sequences 1 (accession number NC_001879 position 96811 to 97844), 2 (position 95356 to 96811) and 3 (position 93132 to 95351) for homologous recombination are underlined. The chimeric aadA gene is inserted within the ycf2 essential gene at position 95351 of the tobacco plastid genome. The chimeric *A. thaliana* ppo gene is inserted into the intergenic region between plastid genes ndhB and trnL at position 96811 of the tobacco plastid genome. Components of the chimeric *A. thaliana* ppo gene are the maize plastid 16S PEP-NEP rRNA gene promoter fused to the *N. tabacum* plastid rbcL RBS (PmrrN), the *A. thaliana* ppo gene (Atppo) and the *N. tabacum* plastid rps16 3'UTR (3'rps16). Components of the chimeric aadA gene are *N. tabacum* psbA promoter (PpsbA) fused to aadA, aadA coding sequence (aadA) and the *A. thaliana* psbA 3'UTR (3'psbA). The restriction sites marked for: EcoRI, EcoRV, MluI, NcoI, NdeI, NgoMIV, ScaI, SnaBI, SpeI, XbaI and XhoI.
Figure 4:
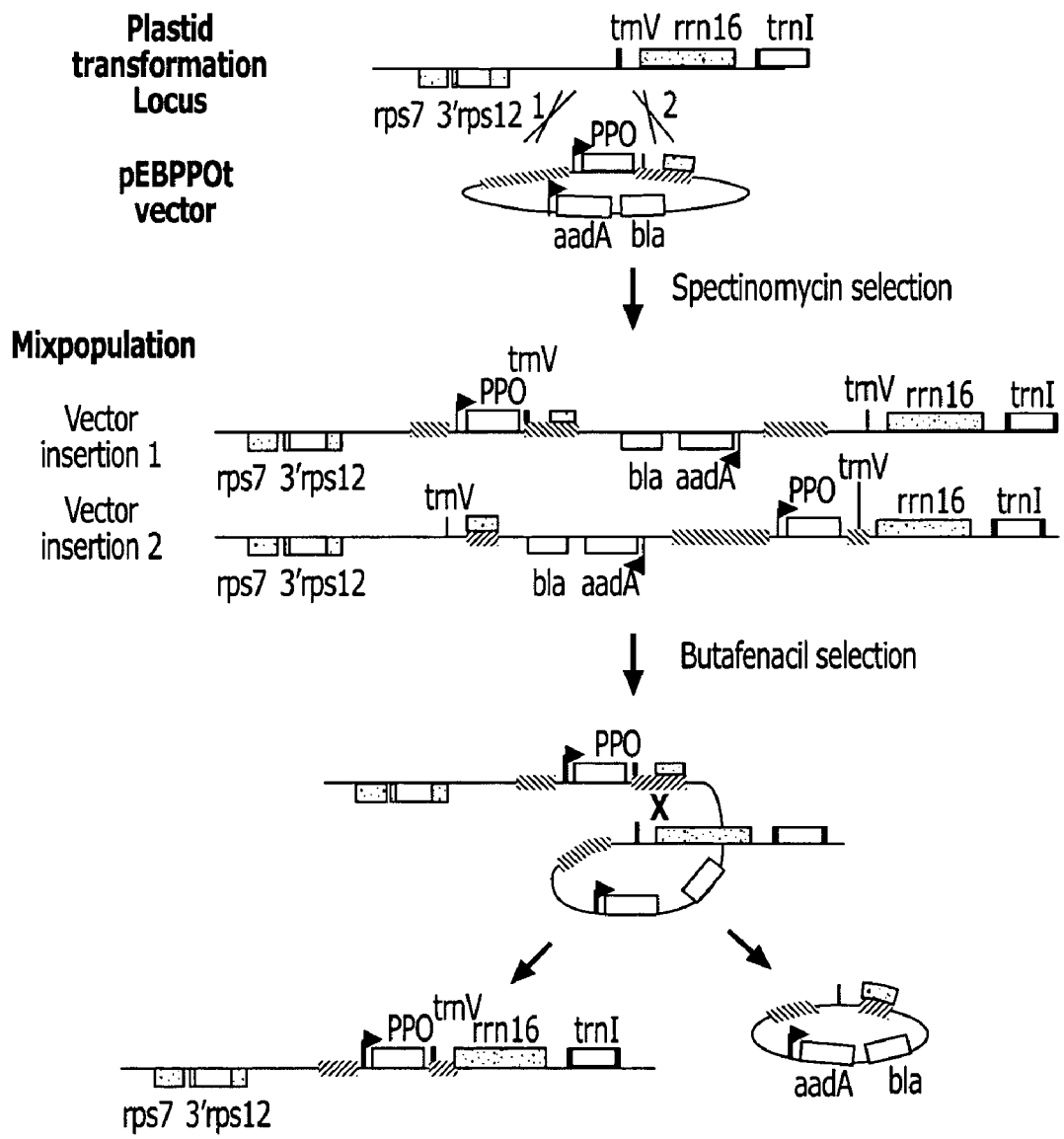
FIG. 4. illustrates a scheme for integration of PPO transgene into a plastid genome. Upon initial spectinomycin selection, the complete vector integrates the plastid genome via two possible recombination events occurring between the vectors chloroplast rps12 (1) or trnV-rrn 16 flanking sequences (2) and the plastid targeted locus. These single crossovers events creates a mix population of plastid transformed genomes having the vector inserted in different conformation. Subsequent, butafenacil selection allows second recombination event between direct repeated sequences that results in stable integration of the PPO gene in the plastid genome and complete excision of aadA with the vectors backbone sequence. Only one of two possible intra-recombination events is shown in the present example. Continuing butafenacil selection allows homoplasmic sorting for plastid genomes containing the PPO gene.
Figure 5A:
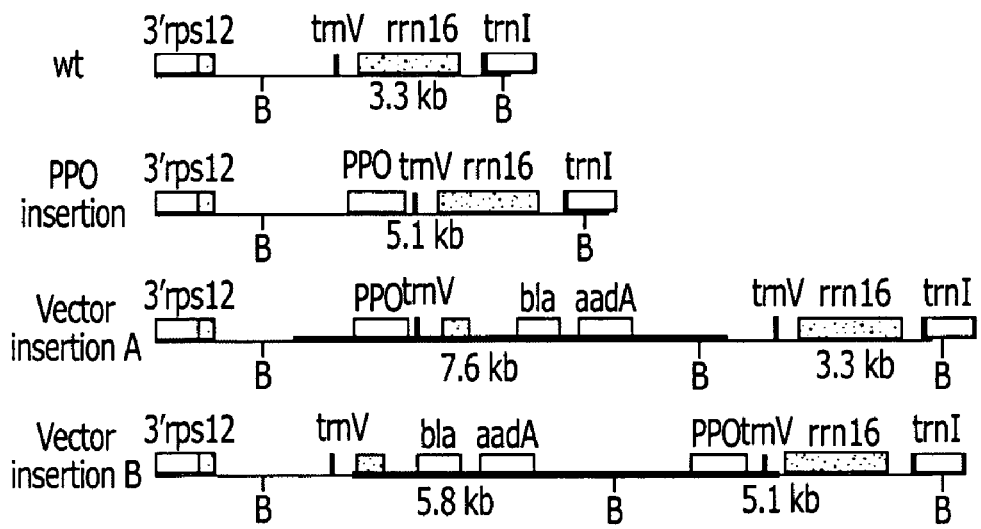
FIG. 5. Examples of Southern hybridization analysis to identify homoplasmic plastid transformants. A) BamHI length polymorphisms expected between wild type transformation locus, PPO transformed plastids and complete vector integration after single cross-over recombination event between the rps12 flanking sequences (1) or the trnV-rrn16 flanking sequences (2). B indicates position of BamHI restriction sites. B) Upper panel; Southern hybridization hybridization of BamHI digested total DNA from wild type (lane wt) and 10 transformants (lanes marked 1 to 10) and hybridized with probe specific to insertion locus. Wild type plastid sequence is observed at 3.2 kb, homoplasmic PPO transformed lines (lanes 1–3, 5–7 and 10) sequence at 5.0 kb. Heteroplasmic line (lanes 4 and 9) contain both PPO insert and wild type sequences. Lower panel; Southern hybridization hybridization of SpeI digested total DNA from wild type (lane wt) and 10 transformants (lanes marked 1 to 10) and hybridized with aadA gene specific probe. The aadA gene (0.9kb) is only observed in the heteroplasmic lines (lanes 4 and 9).
Figure 5B:
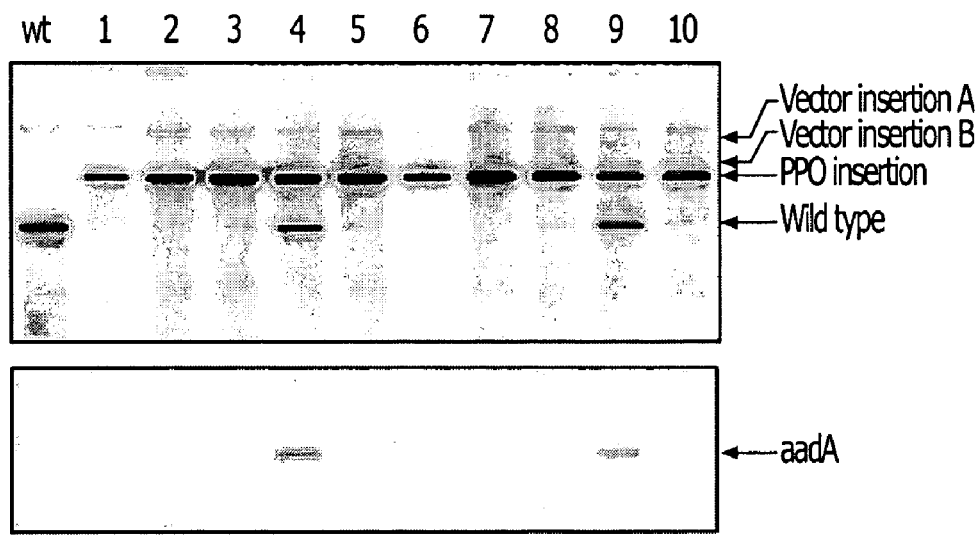
Figure 6:
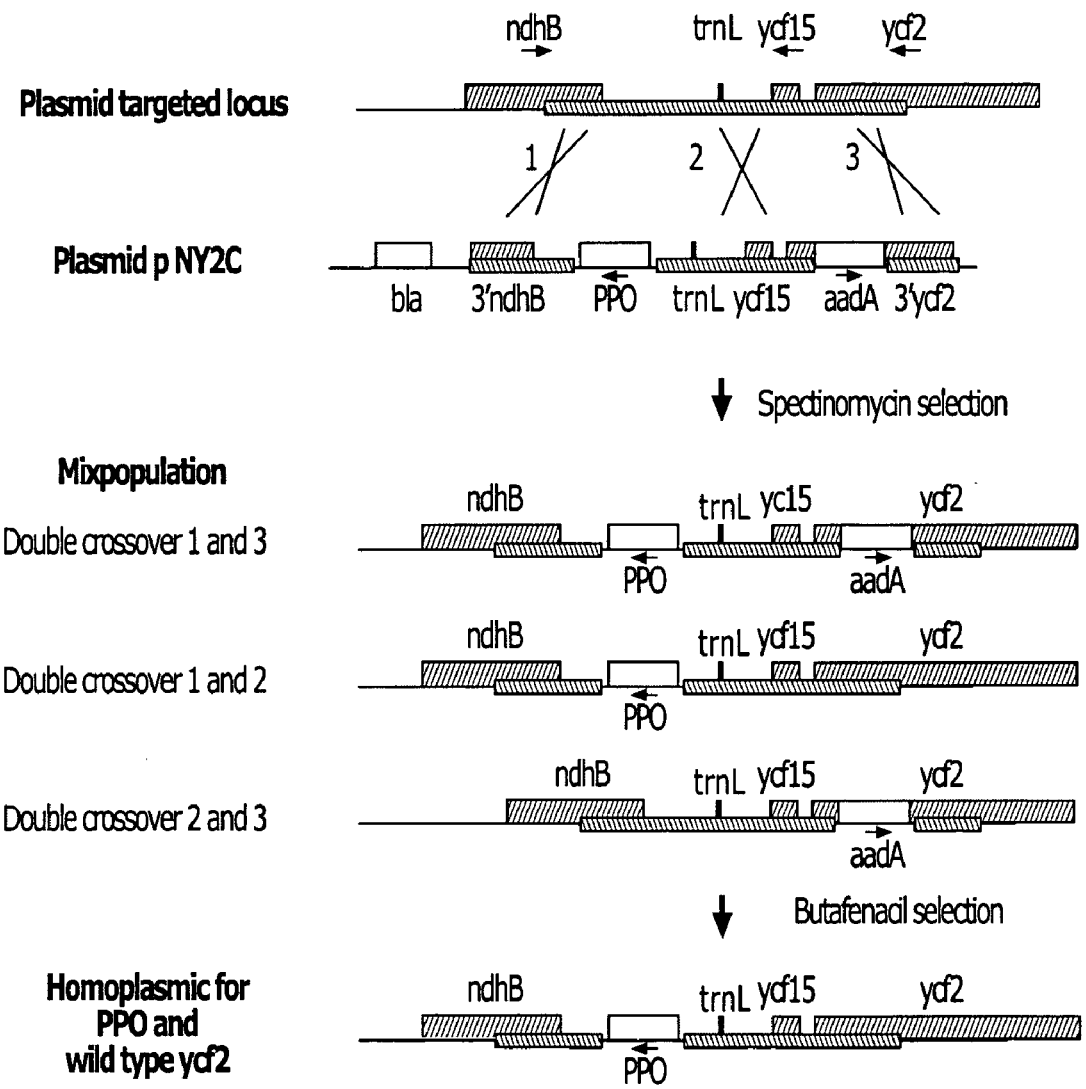
FIG. 6. Illustrates a scheme for integration of PPO transgene into plastid genome. Upon initial spectinomycin selection, selectable markers integrate the plastid genome via 3 possible double crossover recombination events occurring between the plastid transformation vector and the targeted plastid locus. Creating a mix population of plastid transformed genomes having either one or both selectable markers. Subsequent, butafenacil selection allows homoplasmic sorting for plastid genomes containing the PPO gene and complete excision of aadA from the essential gene.
Figure 7:
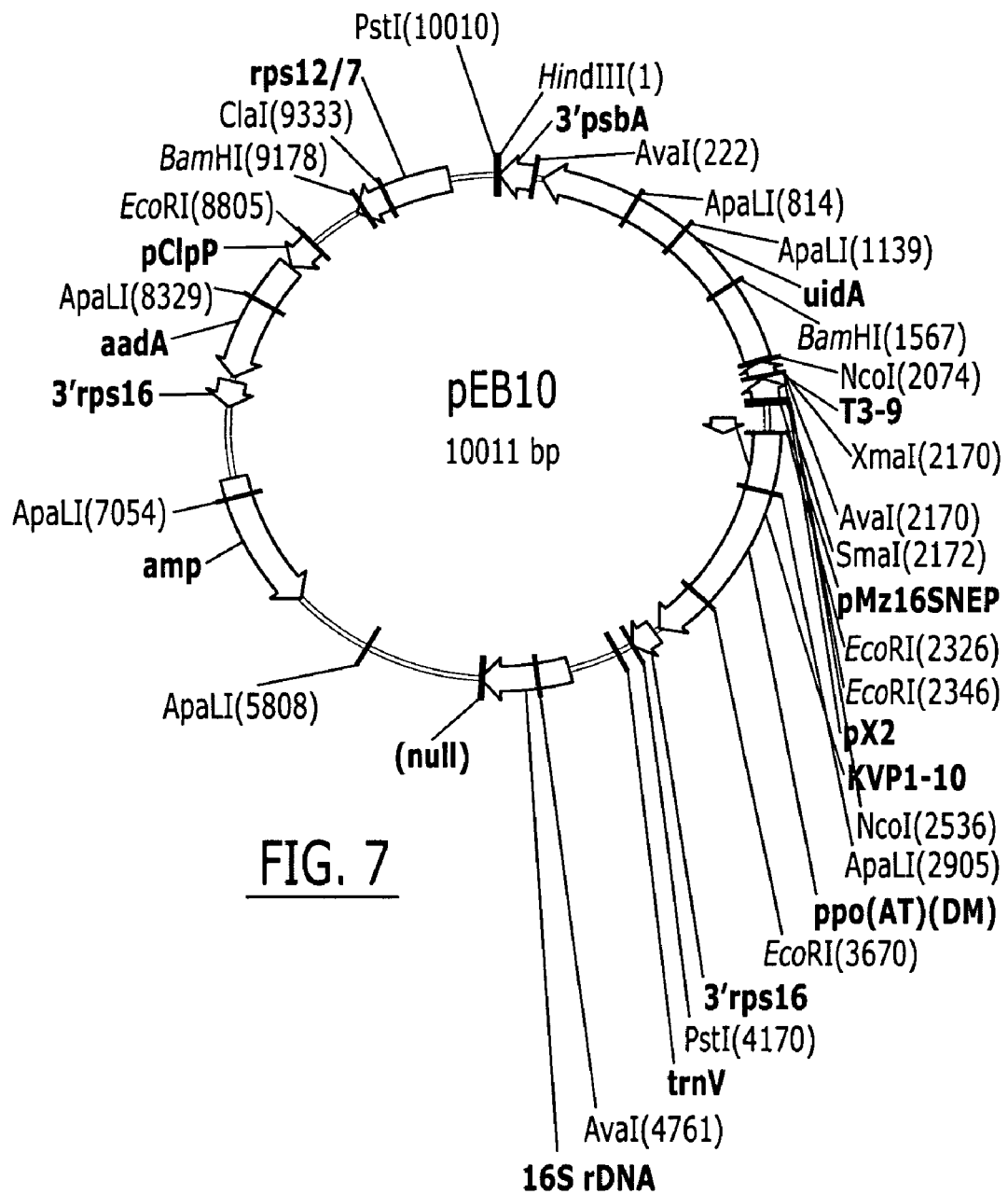
FIG. 7. Map of the pEB10 plastid transformation vector. Plastid targeting sequence plDNA 16rDNA and rps12/7 are represented by hatched lines. Components of the chimeric *A. thaliana* ppo gene are the *Staphylococcus aureus* bacteriophages X2 promoter like-sequences fused to the bacteriophage kvp1 gene 10 5'UTR (PX2k10), the *A. thaliana* ppo gene (Atppo) and the *N. tabacum* plastid rps16 3'UTR (3'rps16). Components of the chimeric aadA gene are the *N. tabacum* clpP plastid promoter (PclpP), the aadA coding sequence (aadA) and the *N. tabacum* plastid rps16 3'UTR (3'rps16). The vectors ampicilline resistance gene (amp) is indicated by arrow. The restriction sites marked for are PstI, NdeI, EcoRI, EcoRV, BamHI and ScaI.

The plasmid pEBNY2+aadA was linearized with NdeI restriction endonuclease. The chimeric ppo gene was removed from pEBPPO cutting it with PstI restriction endonuclease. Following the restriction digestions the ends the 8.6 kb NdeI linearized pEBNY2+aadA plasmid and the 1.8 kb PstI fragment containing the chimericppo gene were rendered blunt with the T4 DNA polymerase. Subsequently, these fragments were ligated together to yield the plasmid pNY2C (SEQ ID NO:3, FIG. 3). Plasmids having the chimeric ppo gene in either orientation were obtained but only the one having ppo oriented in the same direction as the ycf2 gene was retained.

Example 5

Biolistic Transformation of the Tobacco Plastid Genome with pNY2C and Selection (see Example 6 for a Detailed Description of the Transformation and Selection Method)

After delivery of the vector DNA into the plastid, transformants are selected for spectinomycin resistance, which is conferred by the aadA gene integrated into the essential ycf2 gene. The plastid sequences flanking both selectable marker genes within the plastid transformation vector provides 3 different recombination loci and different combinations of double crossover events will produce a mix population of transformed plastid genomes having either one or both selectable markers. Switching to butafenacil selection will result in the segregation of the mixed plastid genome population and the selection of homoplasmic plastids expressing the ppo gene. The natural selective pressure will favor the wild-type copy of the essential gene and will thus result in the complete loss of the aadA gene.

PCR analysis of DNA samples from events obtained from initial spectinomycin selection showed that both, the aadA and the ppo genes are present in the transformants. Subsequently, after two to three rounds of subculture on butafenacil, PCR analysis of DNA samples from the same events confirmed the loss of the aadA gene while the ppo gene is retained in the transformants.

Southern blot analysis was used to demonstrate that the ppo gene could be inserted into the plastid genome and that homoplasmic cells were obtained upon butafenacil selection. Total cellular DNA from 20 transformants that were subjected to three or four subculture rounds on butafenacil containing medium was analyzed by Southern blot hybridization. The DNA from wild-type and transformants was digested with NcoI and hybridized with a DNA probe specific to tobacco plastid sequence (NC_001879, positions 96811 to 97844). This probe, which normally recognizes a 2.6 kb NcoI fragment in the wild-type, predominately hybridized with a 4.4 kb DNA fragment in all of the transformants, indicating that the 1.8 kb ppo gene is stably inserted into the plastome and that homoplasmic transformants have been selected in these events.

Southern blot analysis also revealed that aadA insertion into the essential ycf2 gene upon spectinomycin selection is unstable. Southern analysis from DNA samples taken from those 20 transformants after initial selection on spectinomycin containing medium which were described above indicated that the aadA chimeric gene was inserted into the targeted essential plastid gene but that the cells remained in the heteroplasmic state as a certain portion of wild-type copies was retained. A tobacco plastid DNA probe (NC_001879 position 94408 to 95861) specific for the aadA plastid-targeting locus hybridized to both the wild-type 1.4 kb fragment and a 2.6 kb fragment containing the aadA insertion in every transformants. After several rounds on butafenacil selection the probe only recognized the 1.4 kb wild-type DNA fragment indicating that all the genomes reverted to the wild-type and that the aadA gene was lost when the spectinomycin selection pressure was removed. Furthermore, no hybridization signal was observed when the Southern blot was hybridized with an aadA specific probe.

Example 6

Plastid Transformation and Selection

I. Seed Germination

Tobacco (*Nicotiana tabacum*) seeds are sterilized with 70% ethanol for several minutes, rinsed three to five times with sterile water, and then plated onto germination media (Table 2, 3). Germination plates are incubated at around 25° C. with 12–16 hours photoperiod. The Germination medium (GM) is as follows: MS Macro-salts ½×; MS Micro-salts 1×; GM vitamins (100×) 10 ml/L; $Na_2EDTA$ 75 mg/L; $FeCl_3$ $6H_2O$ 27 mg/L; Sucrose 10 g/L; Phytagar 8 g/L; and pH adjusted to 5.5.

The GM vitamins (100×) are mixes as follows: Inositol 10 g/L; Biotin 5 mg/L; Pyridoxine 50 mg/L; Thiamine 50 mg/L; Nicotinic Acid 500 mg/L; Folic Acid 50 mg/L; and Glycine 200 mg/L.

II. Explant Preparation and DNA-Delivery

Leaves of approximately 2 week old tobacco seedlings are placed with the adaxial side ("upper side") up in the center of plates containing tobacco culture medium (Table 4) Alternatively the vitamins in this medium can be replaced by 100 mg/L inositol and 1 mf/L thiamine. The particle bombardment is performed on the same day. The Tobacco culture medium is as follows: MS Salts 1×; MS Vitamins ½×; B5 Vitamins ½×; BAP 1 mg/L; NAA 0.1 mg/L; Sucrose 30 g/L; and Sigma purified agar 6 g/L with the pH adjusted to 5.8.

DNA-particle preparation is performed as follows: 60 mg of particles (tungsten or gold) are sterilized with 0.5 ml of 70% ethanol, washed twice with 0.5 ml sterile double distilled water, and then resuspended in 1 ml of 50% glycerol. To a 100 µl aliquot of the particle suspension, 10 µg of DNA, 100 µl of 2.5M $CaCl_2$, 50 µl of 0.1 M spermidine is added sequentially and mixed gently with each adding. The DNA coated particles are centrifuged briefly, followed by one wash with 200 µl of 70% ethanol and another wash with 200 µl of 100% ethanol. Then they are resuspended in 100 µl of 100% ethanol. For each bombardment, 5 to 10 µl of DNA-particles are used.

The bombardment is carried out using the PDS 1000 Helium gun (Bio-Rad, Richmond, Calif.), following a modification of the protocol described by the manufacturer. Plates with the target explants are placed on the third shelf from the bottom of the vacuum chamber, bombarded with 650 p.s.i. rupture disks with single or multiple shots per plate.

III. Selection of Homoplasmic Transplastomic Plants Expressing the ppo Gene in their Plastids a) Initial Selection The initial selection is carried out with spectinomycin as the selection agent, or with the combination of spectinomycin and Formula XVII in the case of dual selection. Spectinomycin is added at 500 mg/L to tobacco culture media in either case, while Formula XVII is added in the media at concentrations of about 2 nM to about 10 nM, preferably about 5 nM to about 25 nM or alternatively, about 25 to about 50 nM.

One week after the bombardment, the explants are transferred to tobacco culture media containing the selection agent(s), with the bombarded sides directly contacting the selection medium. When Formula XVII is included in the selection media, it is preferred to cut the explants into small pieces, to facilitate more efficient selection. After about two to four weeks of selection on spectinomycin containing medium, the explants or, if identifiably, the resistant transformants are carried further to the next phase of the selection to obtain homoplasmic plants expressing the ppo gene in their plastids.

The selection phenotype of the dual selection system is notably different from the phenotype obtained with sole spectinomycin selection. With the sole spectinomycin selection, the selection phenotype is pigmented green, in which the green pigmented transformants are identified against the white non-transformed tissue. In contrast, on the selection media containing Formula XVII, the transformants always appear as white to yellowish calli, on a background of brown non-transformed tissue.

The selection phenotype with lethal selection compound Formula XVII is particularly important for the selection of those tissue types which would not turn to green under the culture conditions used for the selection. It is more desirable and practicable to select white or yellowish tissue against the brown tissue, as in the case with lethal compound Formula XVII, than select white or yellowish tissue against the white tissue.

b) Secondary Selection of Homoplasmic Events Expressing ppo Gene in the Plastome.

The bombarded explants or the selected primary transformants are transferred to tobacco culture media containing only Formula XVII as the selection agent at concentrations of either about 25 nM to about 50 nM or about 50 nM to about 250 nM for further segregation and selection. The tissues are cut into small pieces during the culture and every subculture thereafter, to ensure better contact of the tissue to the media, and thus more efficient selection. After several rounds of selection, samples of the transformants are collected and analyzed by Southern Blot. Out of ten independent transformants analyzed, eight were confirmed to be homoplasmic transformants having the ppo gene integrated into their plastome but not the aadA gene. The other two events were heteroplasmic containing both genes (Table 1).

IV. Regeneration of Homoplasmic Plants and Expression of the ppo Gene in the Plastids Homoplasmic ppo events are regenerated to form shoots on tobacco culture media containing the selection agent. The concentration of cytokinin in the medium may be doubled to enhance regeneration. The shoots obtained are rooted individually on hormone-free tobacco culture media, with or without the selection agent.

The homoplasmy of each individual plant transferred to the greenhouse was confirmed by southern blotting or PCR. All plants are fertile and exhibit a normal phenotype.

The expression of the ppo gene in homoplasmic plants is evaluated by an ELISA assay. The data obtained were compared to that of tobacco nuclear transformants expressing the ppo gene in the nucleus. The ELISA assay demonstrated a significant increase of the PPO protein concentration in the transplastomic plastid plants compared to nuclear transformants (Table 5).

TABLE 1

Quantification of the PPO protein in homoplasmic transplastomic plants and in nuclear transformants expressing the ppo gene.

| Plastid Event Number | PPO protein per total protein [ng/mg] | Nuclear event number | PPO protein per total protein [ng/mg] |
| --- | --- | --- | --- |
| 814 | 127.12 | 2200 | 6.0 |
| 815 | 138.43 | 2203 | 2.4 |
| 816 | 147.72 | 2212 | 0.1 |
| 818 | 143.90 | 2213 | 2.6 |

Example 7

Tomato Plastid Transformation

Syngenta elite tomato genotype ZTV840 was used for plastid transformation. Seed sterilization, germination and the leaf bombardment were performed as previously described for tobacco plastid transformation (Example 6).

Two days after the bombardment, the tomato leaves were transferred to the selection medium with 500 mg/L spectinomycin, and cultured in dim light. One month later, the leaves were cut into small pieces and subcultured to the same selection medium. Transplastomic events bega to appear after two months of the selection. Two events were obtained from 10 plates bombarded with a stable aadA-PPO construct, and another two events from 11 plates bombarded with the transient aadA: stable PPO construct (pEBPPOt).

When the four events just showed up, they consisted of very friable, soft calli with a little bite of green color. These events were then transferred to medium containing 50 to 75 nM of Formula XVII for the second selection phase. Three of the four events survived Formula XVII selection and continued to grow on the selection media for more than six months.

Example 8

High Level of Herbicide Tolerance Obtained with Homoplasmic PPO Transplastomic Plants Much higher levels of herbicide tolerance is obtained with transplastomic homoplasmic plants expressing ppo in their plastids than with ppo expressing nuclear transformants. PPO transplastomic tobacco plants were survived very well with Formula XVII treatmentup to the concentration of 2000 nM, the highest herbicide level tested, while in the same study nuclear transformants showed sensitivity when they were treated with Formula XVII at a concentration above 100 nM.

Example 9

Expression of Transgenes in Plastids Using Novel Promoter sequence might be able to function as plastid gene translation element. The bacteriophage T7 gene 10 5'UTR sequence, which contains a SD element, was previously shown to be very efficient in promoting translation in plastids (McBride et al., (1994) Proc. Natl. Acad. Sci. 91: 7301–7305; Ye et al., (2001) Plant J. 25: 261–270; Kuroda and Maliga (2001) Nucl. Acids Res. 29: 970–975). The following sequence from Kluyvera bacteriophage gene 10 and T3 bacteriophage gene 9 were tested for their ability to act as 5'UTR sequences for plastid gene expression.

```
SEQ ID NO:16 Kluyvera Bacteriophage kvp1 gene 10 5'UTR
tctagaGACA TTACGTTCTC CCCTTGAGTG ATACACAATG AGAACCAACT CGTTTCAAGT   60

AGTACCTCAC ATAACTTATC TTTTAAATCA ACAGAAGGAG ATTCAcCatg                110

SEQ ID NO:17 Bacteriophage T3 gene 9 5'UTR
tctagAGGGA GACCTCATCT TTGAAATGAG CGATGACTAA AGGTTGGAGT CCTTTGGTTT   60

CCCTTTATCT TTAATAACTT AGGAGATTTA ATtcatg                              97
```

The following invention provides nucleic acid sequences of non-plastid origin useful for the expression of transgenic genes in plastids. There are only a limited number of gene regulatory elements such as promoters, 5'untranslated region (5'UTR) and 3'untranslated region (3'UTR) available for plastid transgene expression and most of them are plastid sequences. As plastid genomes are highly active in homologous recombination, the insertion in the genome of endogeneous sequences as regulatory element could bring about genomic rearrangements resulting in loss or inactivation of the transgenic function. In order to prevent such genomic rearrangement, foreign sequences sharing little homology with plastid genomic DNA sequence should be used as regulatory elements for plastid transgen; expression.

New Promoter

The *Staphylococcus aureus* bacteriophages X2 promoter like-sequence, which was reported to be able to promote gene expression in *E. coli*. (Carbonelli et al., FEMS Micro. Letters 177:75–82, 1999), was tested for its ability to promote gene expression in tobacco plastids. The X2 sequence (SEQ 10) contains bacteria type promoter features such as canonical hexanucleotide—10 region (TATAAT) and—35 region (TTGCTG) and a—16 promoter box (TRTG), that is also observed in many chloroplast PEP promoters. The X2 sequence (position 141 to 219 from published sequence) was linked to the to a 5'untranslated sequence functional in plastid and fused to a reporter gene in a tobacco plastid transformation vector.

Making of plastid transformation vector having PPO has selectable marker which is under the control of the bacteriophage X2 promoter Amplification of the bacteriophage kvp1 gene 10 5' UTR The kvpI gene 10 5 'UTR was isolated by PCR amplification from a plasmid containing kvp1 gene 10 using a top strand primer comprising an introduced XbaI restriction site at the 5'end of the 5'UTR region (5' GTTCTAGAGACATTACGTTCTCCCCTTG 3' (XbaI site is underline) SEQ ID NO:28) and a bottom strand primer comprising an introduced NcoI restriction site overlapping the ATG initiation codon (5' AGATATCCATGGTGAATCTCCTGTTGATT 3' (NcoI restriction site is underline) SEQ ID NO:29). PCR amplification of a 119 bp fragment was performed with taq DNA Polymerase kit (QIAGEN, Valencia Calif.) in a Perkin Elmer Thermal Cycler 480 according to the manufacturer's recommendations (Perkin Elmer/Roche, Branchburg. N.J.) as follows 5 min 95° C., followed by 5 cycles of 1 min 95° C./1 min 40° C./15 sec 72° C., then 25 cycles of 1 min 95° C./1 min 55° C./15 sec 72° C.

Plasmid pEBPKVP-10 was created by ligating together the 105 bp XbaI-NcoI fragment from the kvp1 gene 10 5'UTR amplified fragment with an 8.0 kb XbaI-NcoI fragment from pEBPaccD vector. Plasmid pEBPKVP10-GFP was created by ligating a 5.2 kb NcoI-BamHI fragment from pEBPKVP10 with a 1.8 Kb fragment from pPB69b, containing green fluorescent protein (GFP) gene linked to the *A.*

```
SEQ ID NO:15 Staphylococcus aureus bacteriophage X2 promoter
GTTAAAGAAT GTAGCTGACT GCATACTTAA ACCACCCATA CTAGTTGCTG GGTGGTTTTT   60

ATGTTATAAT ATAAATGTG                                                   79
```

New 5'Untranslated Region with Shine-Dalgarno Like Sequence

In land plant plastids, the mRNA 5'UTR sequences are essential for mRNA stability and translation initiation process. The 5 'UTRs of most highly expressed plastid genes contain a Shine-Dalgarno like sequence that is complimentary to the 3'end of the plastid 16S rRNA and is believed to play a predominant role in translation initiation. It is possible that foreign sequences that contain a Shine-Dalgarno like

*thaliana* plastid psbA 3 'UTR. The maize 16S NEP-PEP promoter was amplified by PCR from pPB98 using a top strand primer comprising an introduced EcoRI restriction at the 5' end of the 16S rRNA gene promoter region (5' GCCAGAATTCACCACGATCGAACGGGAATGGATA 3' (EcoRI site is underline)) (SEQ ID NO:20) and a bottom strand primer comprising an introduced XbaI restriction site at the 3' end of the 16S rRNA gene promoter region (5' CTCTAGAGATTCGGAATTGTCTTTCCTT 3' (XbaI restriction site is underline) SEQ ID NO:21). PCR amplification of a 164 bp fragment was performed with the Pfu Turbo DNA polymerase kit (Stratagene, LaJolla Calif.) in a Perkin Elmer Thermal Cycler 480 according to the manufacturer's recommendations (Perkin Elmer/Roche, Branchburg. N.J.) as follows 5 min 95° C., followed by 35 cycles of 1 min 95° C./1 min 50° C./15 sec 72° C.

The amplified 16S rRNA promoter sequence was cut with XbaI and EcoRI and the resulting 152 bp fragment was ligated to a 6.0 kb XbaI-EcoRI fragment from pB98 plastid transformation vector. The resulting plasmid was subsequently cut with XbaI and BamHI and a 5.1 kb fragment isolated from the digest was ligated with a 1.9 kb XbaI-BamHI fragment from pEBPKVP10-GFP, containing the kvp1 gene 10 5'UTR::GFP ::*A.thaliana* psbA 3'UTR chimeric, to give pEBZM16SKGFP.

Construction of Plasmid RTK7 having

The 116 bp bacteriophage T3 gene 5'UTR was PCR amplified from a plasmid using a top strand primer (RTK36) comprising an introduced NcoI restriction site at the 3'end of the T3 gene 9 5'UTR (5' GAAGATG<u>CCATGG</u>ATTAA -TCTCCT--GTTATTAAAG 3' (NcoI site is underline) SEQ ID NO:22) and a bottom strand primer (RTK39) comprising an introduced SmaI site at the 5' end of the 5'UTR (5' CGAATCTCTT <u>CCCGGG</u>TAGAGGGAGACCTCATCTTTG 3' (SmaI restriction site is underline)SEQ ID NO:23). A 328 bp fragment having the Maize 16S PEP-NEP rRNA gene promoter and tobacco psbA gene promoter was PCR amplified from pEBT3–9 GFP using a top strand primer (RTK38) comprising an introduced SmaI restriction site at the 3'end of the Maize 16S PEP-NEP promoter (5' CTCCCTCTA <u>CCCGGG</u>AAGAGATTCGGAATTGTCTTTCC 3' (SmaI site is underline)SEQ ID NO:24) and a bottom strand primer (RTK37) comprising an introduced BspHI site at the 3' end of the psbA 5'UTR (5' CGCTTAG <u>TCATGA</u>TAAAATCTTGGTTTATTTAATCATC 3' (BspHI restriction site is underline)SEQ ID NO:25). PCR products were purified, mixed together at equal molar ratio with primers RTK36 and RTK37 and mixture was used to PCR amplify a 421 bp fragment. PCRs were performed with the Pfu Turbo DNA polymerase kit (Stratagene, LaJolla Calif.) in a Perkin Elmer Thermal Cycler 480 according to the manufacturer's recommendations (Perkin Elmer/Roche, Branchburg. N.J.).

To make plasmid RTK7, the plasmid RTK6 having the ppo and gus genes cloned in opposite orientation was first created by ligating a 7.5 kb HindIII-NcoI fragment from pEB8a, the transformation vector with ppo::*N. tabacum* rps16 3'UTR chimeric gene, with a 2.1 kb HindIII-NcoI fragment containing gus::*A.thaliana* psbA 3'UTR gene from plasmid pEBPkvp10. Plasmid RTK7 was eventually made by ligating a NcoI linearized 9.6 kb RTK6 with the 405 bp NcoI-BspHI PCR amplified Maize 16S and psbA promoters. Only the plasmid having psbA promoter driving ppo and Maize 16S PEP-NEP promoter driving gus was retained.

Construction of a Bacteriophage X2 promoter-like sequence fused to the kvp1 gene 10 5'UTR: GFP::*A. thaliana* plastid psbA 3'UTR chimeric gene.

An 85 bp EcoRI-XbaI fragment consisting of the bacteriophage X2 promoter-like sequence was created by annealing together a top stand oligonucleotide (5' AATTCGT-TAAAGAATGTAGCTGACTGCATACTFAAACCACCC-ATACTAGTTGCTG GGTGGT=TTATGTTATAATATAAATGTGT 3') (SEQ ID NO:26) with the following complimentary bottom strand oligonucleotide (5' CTAGACACATTFATATTATAACAT-AAAAACCACCCAGCAACTAGTATGGGTGGTT TAAGTATGCAGTCAGCTACATTCTTTAACG 3')(SEQ ID NO:27). Plasmid PEBX2 was created by ligating the created 85 bp EcoRI-XbaI fragment with a 6.8 kb EcoRI-XbaI fragment from pEBZM16SKGFP plasmid, containing the kvp1 gene 10 5'UTR::GFP ::*A.thaliana* psbA 3'UTR with the remainder of the plastid trnnsformation vector.

Construction of Plastid Transformation Vector pEB10

Plasmid pEB9 was created by ligating a 200 bp BglII-NcoI fragment from pEBX2, containing the X2 promoter-like sequence fused to the kvp1 gene 10 5'UTR, and a 8.5 kb BglII-NcoI from pEB8a plastid transformation vector.

1 AATTCGTTAAAGAATGTAGCTGACTGCATACTTAA-ACCACCCATACTAGT

50 <u>TGCTGGGTGGTTTTTTATGTTATAATATAAATGTGTC-TAGA</u> GACATTACGT

100 TCTCCCCTTG AGTGATACAC AATGAGAACC AACTCGTTTC AAGTAGTACC

150 TCACATAACT TATC=TTAA ATCAACAGAA GGAGATTCAC Catg

DNA sequence of the chimeric the *Staphylococcus aureus* bacteriophages X2 promoter like-sequences fused to the bacteriophage kvp1 gene 10 5'UTR. The X2 sequence is underlined; the initiation codon (ATG) is in small caps. (SEQ ID NO: 18).

The final pEB10 plastid transformation vector was created by ligating a 7.8 kb BglII-HindIII fragment from pEB9 with a 2.3 kb fragment from pRTK7, containing the chimeric gene pMz16SNEP::T3-9 5'UTR:: uidA:: 3'psbA.

Example 10

Plastid Transformation with pEB10

Resulting chimeric reporter gene was stably introduced in tobacco plastid genome using plastid transformation dual selection protocol described in U.S. application case 70149. Out of 6 plastes bombed one event was found to be able to grow on 50 nM of butafenacyl after two rounds of selection on spectinomycin. After 3 rounds of selection on butafenacyl the event was confirmed by Southern analysis to be homoplasmic for insertion in the chloroplast genomes of the PPO and gus genes. Activity of GUS was visualized by standard GUS assays.

The invention claimed is:

1. A method for obtaining a transplastomic plant comprising the steps of:

a) introducing into a plant cell plastid a plastid transformation vector comprising two distinct selectable marker constructs, wherein the first selectable marker construct comprises a promoter functional in a plant cell plastid and a transcriptional termination region functional in a plant cell plastid operably linked to a first selectable marker (a non-lethal marker) that confers resistance to a non-lethal selective compound and the second selectable marker construct comprises a promoter functional in a plant cell plastid and a transcriptional termination region functional in a plant cell plastid operably linked to a second selectable marker (a lethal marker) that confers tolerance to a lethal compound, wherein the second selectable marker construct is flanked by nucleic acid sequences which are homologous to non-essential plastid targeting nucleic acid sequences, and the first selectable marker construct is flanked by nucleic acid sequences which are homologous to essential plastid targeting nucleic acid sequences;

b) placing a plant cell comprising the recombinant nucleic acid molecule on a first culture medium comprising a plastid non-lethal compound to which the first selectable marker confers resistance for either 1) a period of about 2 weeks or 2) or until shoots appear on a callus formed from the plant cell; and c) placing the plant cell on a second culture medium comprising a plastid lethal compound to which the second selectable marker confers resistance for a period of time sufficient to permit the plant cell to be homoplasmic for the lethal marker; and d) obtaining a transplastomic plant by regenerating the transplastomic plant from the plant cell, wherein the transplastomie plant does not comprise the first selectable marker.

2. The method of claim 1, wherein the first selectable marker is unstably or transiently integrated into the plastome.

3. The method of claim 1, wherein the first selectable marker is an antibiotic resistance gene.

4. The method of claim 3, wherein the antibiotic resistance gene is aadA and the non-lethal selective compound is spectinomycin or streptomycin.

5. The method of claim 1, wherein the second selectable marker is a herbicide tolerance gene.

6. The method of claim 5, wherein the herbicide tolerance gene is a mutated form of a protoporphorynogen oxidase (ppo) and the lethal selective compound is butafenacil or Formula XVII.

7. The method of claim 1, wherein the plastid transformation vector further comprises one or more gene constructs of interest expressible in plastids and encoding one or more gene products of interest, and wherein the one or more gene constructs of interest are adjacent to the second selectable marker construct on the vector.

8. The method of claim 7, wherein the second selectable marker construct and the one or more gene constructs of interest each have different promoters functional in plastids and are expressed independently.

9. The method of claim 7, wherein the second selectable marker construct and the one or more gene constructs of interest are organized as a operon-like polycistronic gene.

10. The method of claim 1, wherein the plastid transformation vector comprises SEQ ID NO:3.

11. The method of claim 1, wherein the plant is tobacco, tomato, petunia, potato, brassica spp., safflower, or lemna.

* * * * *

UNITED STATES PATENT AND TRADEMARK OFFICE
CERTIFICATE OF CORRECTION

PATENT NO.       : 7,235,711 B2
APPLICATION NO.  : 10/680824
DATED            : June 26, 2007
INVENTOR(S)      : Boudreau et al.

Page 1 of 1

It is certified that error appears in the above-identified patent and that said Letters Patent is hereby corrected as shown below:

Under Related U.S. Application Data, on the Title page of the patent, please correct (60) as follows:

(60) Provisional application No. ~~60/425,331, filed on Nov. 12, 2002, provisional application No.~~ 60/418,596, filed on Oct. 15, 2002.

Signed and Sealed this

Nineteenth Day of February, 2008

JON W. DUDAS
*Director of the United States Patent and Trademark Office*

SEQUENCE LISTING

<160> NUMBER OF SEQ ID NOS: 29

<210> SEQ ID NO 1
<211> LENGTH: 7652
<212> TYPE: DNA

<213> ORGANISM: Artificial Sequence
<220> FEATURE:
<223> OTHER INFORMATION: pEBPPOt plastid transformation vector
      (Example 1 VII).

<400> SEQUENCE: 1

```
cttttgctct gcacggaaac taaaccatct ggagtctcat atgttaagtt gtatcctccg     60
ctctccagct tagtgatacc taagagcttc aagacaact taactttgct acctaatctt    120
gcagatattg cttctggcaa cattcgaagt cccttcctga agaaccaac tgtttggccc    180
tgtggttttg gcaggcgcgg gtctcgttct gccttgggag cgttttcct ctcctgaatt    240
gccttaaaag taccacctat tatgcttcca ccattttgct ctagtttcca aaccttccca    300
aacgctgctt tcatgctcag ttttgaagga tcaccagcat aaacacctga acaaaacggt    360
tcaatcaggc gctcaaaaac ctcatcaccg aggttacgcc gtacaaactc ctccacagat    420
tcttcacgac ctggaggtga cggtcgaatg ccaagtgcac caaaaccagc tctaatcttc    480
ccaccaatac tcatcaaatc aaagaacggt aagtctgtta gcttcgatgg aaccggcctc    540
aatttcccat tccacaacac aaaccttggc gcagtaggct ctcccaacac caaatcatcc    600
ttcaaaccac tatctaccac catagtgagc ataggatcag acggttgaaa actattggga    660
ccttcttccc agagaaaacc attctcttca cgagtgataa tgttgcctcc aacacgatcc    720
ttagcctcgg tcacaattaa attcggagca gcatcaggat gcttagtagc aagcgcctga    780
gcgatgcaaa gaccactaat acctccgccg acaatcacac aatccatgaa tccctccta    840
caactgattc ggaattgtct ttccttccaa ggataacttg tatccaggcg cttcagatta    900
ttagcctgga gttcgccacc agcagtatag ccaaccctac cctatcacgt caatcccaca    960
agcctcttat ccattcccgt tcgatcgtgg tgaattagct tctgcagtcg cactattacg   1020
gatatgaaaa taatggtcaa aatcggattc aattgtcaac tgcccctatc ggaaatagga   1080
ttgactaccg attccgaagg aactggagtt acatctcttt tccattcaag agttcttatg   1140
cgtttccacg cccctttgag accccgaaaa atggacaaat tccttttctt aggaacacat   1200
acaagattcg tcactacaaa aaggataatg gtaaccctac cattaactac ttcatttatg   1260
aatttcatag taatagaaat acatgtccta ccgagacaga atttggaact tgctatcctc   1320
ttgcctagca ggcaaagatt tacctccgtg gaaaggatga ttcattcgga tcgacatgag   1380
agtccaacta cattgccaga atccatgttg tatatttgaa agaggttgac ctccttgctt   1440
ctctcatggt acactcctct tcccgccgag cccttttct cctcggtcca cagagacaaa   1500
atgtaggact ggtgccaaca attcatcaga ctcactaagt cgggatcact aactaatact   1560
aatctaaatat aatagtctaa tatatctaat ataatagaaa atactaatat aatagaaaag   1620
aactgtcttt tctgtatact ttccccggtt ccgttgctac cgcgggcttt acgcaatcga   1680
tcggattaga tagatatccc ttcaacatag gtcatcgaaa ggatctcgga gacccaccaa   1740
agtacgaaag ccaggatctt tcagaaaacg gattcctatt caaagagtgc ataaccgcat   1800
ggataagctc acactaaccc gtcaatttgg gatccaaatt cgagattttc cttgggaggt   1860
atcgggaagg atttcgtacc caattcgccc tatagtgagt cgtattacaa ttcactggcc   1920
gtcgttttac aacgtcgtga ctgggaaaac cctggcgtta cccaacttaa tcgccttgca   1980
gcacatcccc ctttcgccag ctggcgtaat agcgaagagg cccgcaccga tcgcccttcc   2040
caacagttgc gcagcctgaa tggcgaatgg cgcgacgcgc cctgtagcgg cgcattaagc   2100
gcggcgggtg tggtggttac gcgcagcgtg accgctacac ttgccagcgc cctagcgccc   2160
```

```
gctcctttcg ctttcttccc ttcctttctc gccacgttcg ccggaattcg aatagatcta    2220
catacacctt ggttgacacg agtatataag tcatgttata ctgttgaata acaagccttc    2280
cattttctat tttgatttgt agaaaactag tgtgcttggg agtccctgat gattaaataa    2340
accaagattt taccatgagg gaagcggtga tcgccgaagt atcgactcaa ctatcagagg    2400
tagttggcgt catcgagcgc catctcgaac cgacgttgct ggccgtacat ttgtacggct    2460
ccgcagtgga tggcggcctg aagccacaca gtgatattga tttgctggtt acggtgaccg    2520
taaggcttga tgaaacaacg cggcgagctt tgatcaacga ccttttggaa acttcggctt    2580
cccctggaga gagcgagatt ctccgcgctg tagaagtcac cattgttgtg cacgacgaca    2640
tcattccgtg gcgttatcca gctaagcgcg aactgcaatt tggagaatgg cagcgcaatg    2700
acattcttgc aggtatcttc gagccagcca cgatcgacat tgatctggct atcttgctga    2760
caaaagcaag agaacatagc gttgccttgg taggtccagc ggcggaggaa ctctttgatc    2820
cggttcctga acaggatcta tttgaggcgc taaatgaaac cttaacgcta tggaactcgc    2880
cgcccgactg ggctggcgat gagcgaaatg tagtgcttac gttgtcccgc atttggtaca    2940
gcgcagtaac cggcaaaatc gcgccgaagg atgtcgctgc cgactgggca atggagcgcc    3000
tgccggccca gtatcagccc gtcatacttg aagctagaca ggcttatctt ggacaagaag    3060
aagatcgctt ggcctcgcgc gcagatcagt tggaagaatt tgtccactac gtgaaaggcg    3120
agatcaccaa ggtagtcggc aaataatgtc taacaattcg ttcaaactag aactagttag    3180
tgttagtcta aatctagttt agtaaaaaac gagcaatata agccttcttt aaataagaaa    3240
gagggcttat attactcgtt tttttctata aaaatgagca aattttata gagtatcata    3300 ttttacttta tttattatat taataataaa taataataat aaataataaa aaattactat    3360
atatttttta ttagaagctc cggctttccc cgtcaagctc taaatcgggg gctcccttta    3420
gggttccgat ttagtgcttt acggcacctc gaccccaaaa aacttgatta gggtgatggt    3480
tcacgtagtg ggccatcgcc ctgatagacg gttttcgcc ctttgacgtt ggagtccacg    3540
ttctttaata gtggactctt gttccaaact ggaacaacac tcaaccctat ctcggtctat    3600
tcttttgatt tataagggat tttgccgatt tcggcctatt ggttaaaaaa tgagctgatt    3660
taacaaaaat ttaacgcgaa ttttaacaaa atattaacgt ttacaatttc ccaggtggca    3720
cttttcgggg aaatgtgcgc ggaaccccta tttgtttatt tttctaaata cattcaaata    3780
tgtatccgct catgagacaa taaccctgat aaatgcttca ataatattga aaaaggaaga    3840
gtatgagtat tcaacatttc cgtgtcgccc ttattccctt ttttgcggca ttttgccttc    3900
ctgtttttgc tcacccagaa acgctggtga agtaaaaga tgctgaagat cagttgggtg    3960
cacgagtggg ttacatcgaa ctggatctca acagcggtaa gatccttgag agttttcgcc    4020
ccgaagaacg ttttccaatg atgagcactt taaagttct gctatgtggc gcggtattat    4080
cccgtattga cgccgggcaa gagcaactcg gtcgccgcat acactattct cagaatgact    4140
tggttgagta ctcaccagtc acagaaaagc atcttacgga tggcatgaca gtaagagaat    4200
tatgcagtgc tgccataacc atgagtgata acactgcggc caacttactt ctgacaacga    4260
tcggaggacc gaaggagcta accgcttttt tgcacaacat ggggggatcat gtaactcgcc    4320 ttgatcgttg ggaaccggag ctgaatgaag ccataccaaa cgacgagcgt gacaccacga    4380
tgcctgtagc aatggcaaca acgttgcgca actattaac tggcgaacta cttactctag    4440
cttcccggca acaattaata gactggatgg aggcggataa agttgcagga ccacttctgc    4500
gctcggccct tccggctggc tggtttattg ctgataaatc tggagccggt gagcgtgggt    4560
```

```
ctcgcggtat cattgcagca ctggggccag atggtaagcc ctcccgtatc gtagttatct   4620
acacgacggg gagtcaggca actatggatg aacgaaatag acagatcgct gagataggtg   4680
cctcactgat taagcattgg taactgtcag accaagttta ctcatatata ctttagattg   4740
atttaaaact tcatttttaa tttaaaagga tctaggtgaa gatcctttt gataatctca    4800 tgaccaaaat cccttaacgt gagttttcgt tccactgagc gtcagacccc gtagaaaaga   4860
tcaaaggatc ttcttgagat cctttttttc tgcgcgtaat ctgctgcttg caaacaaaaa   4920
aaccaccgct accagcggtg gtttgtttgc cggatcaaga gctaccaact cttttccga    4980 aggtaactgg cttcagcaga gcgcagatac caaatactgt ccttctagtg tagccgtagt   5040
taggccacca cttcaagaac tctgtagcac cgcctacata cctcgctctg ctaatcctgt   5100
taccagtggc tgctgccagt ggcgataagt cgtgtcttac cgggttggac tcaagacgat   5160
agttaccgga taaggcgcag cggtcgggct gaacggggg ttcgtgcaca cagcccagct    5220
tggagcgaac gacctacacc gaactgagat acctacagcg tgagctatga aaagcgcca    5280 cgcttcccga aggagaaag gcggacaggt atccggtaag cggcagggtc ggaacaggag    5340
agcgcacgag ggagcttcca gggggaaacg cctggtatct ttatagtcct gtcgggtttc   5400
gccacctctg acttgagcgt cgatttttgt gatgctcgtc aggggggcgg agcctatgga   5460
aaaacgccag caacgcggcc tttttacggt tcctggcctt ttgctggcct tttgctcaca   5520
tgttctttcc tgcgttatcc cctgattctg tggataaccg tattaccgcc tttgagtgag   5580
ctgataccgc tcgccgcagc cgaacgaccg agcgcagcga gtcagtgagc gaggaagcgg   5640
aagagcgccc aatacgcaaa ccgcctctcc ccgcgcgttg gccgattcat taatgcagct   5700
ggcacgacag gtttcccgac tggaaagcgg gcagtgagcg caacgcaatt aatgtgagtt   5760
agctcactca ttaggcaccc caggctttac actttatgct tccggctcgt atgttgtgtg   5820
gaattgtgag cggataacaa tttcacacag gaaacagcta tgaccatgat tacgccaagc   5880
tcgaaattaa ccctcactaa agggaacaaa agctggagct ccaccgccgc gcccaatcat   5940
tccggataac gcttgcatcc tctgtattac cgcggctgct ggcacagagt tagccgatgc   6000
ttattcccca gataccgtca ttgcttcttc tccgggaaaa gaagttcacg acccgtgggc   6060
cttctacctc cacgcggcat tgctccgtca ggctttcgcc cattgcggaa aattccccac   6120
tgctgcctcc cgtaggagtc tgggccgtgt ctcagtccca gtgtggctga tcatcctctc   6180
ggaccagcta ctgatcatcg ccttggtaag ctattgcctc accaactagc taatcagacg   6240
cgagcccctc ctcgggcgga ttcctccttt tgctcctcag cctacggggt attagcagcc   6300
gtttccagct gttgttcccc tcccaagggc aggttcttac gcgttactca cccgtccgcc   6360
actggaaaca ccacttcccg tccgacttgc atgtgttaag catgccgcca gcgttcatcc   6420
tgagccagga tcgaactctc catgagattc atagttgcat tacttatagc ttccttgttc   6480
gtagacaaag cggattcgga attgtctttc attccaaggc ataacttgta tccatgcgct   6540
tcatattcgc ccggagttcg ctcccagaaa tatagccatc cctgccccct cacgtcaatc   6600
ccacgagcct cttatccatt ctcattgaac gacggcgggg agcaaatcc aactagaaaa    6660 actcacattg gcttaggga taatcaggct cgaactgatg acttccacca cgtcaaggtg    6720
acactctacc gctgagttat atcccttccc cgccccatcg agaaatagaa ctgactaatc   6780
ctaagtcaaa gggtcgagaa actcaacgcc actattcttg aacaacttgg agccgggcct   6840
tctttctgca gttcaatgga agcaatgata aaaaaataca aatagaaaag gaagggagg    6900
```

-continued

```
aaatacaaaa aaatagaaga gaaaagtcat acaaagttat atacaaatga ctaccccct    6960
ttttgtattt ccttaatta tttccttaat tgaatttcgg ttgaactagt ctgggagatt    7020
taatgtttta catttacttg taagcgtacc gtgacatgaa gttgttgacc tcaatcgcgg    7080
tttcatatgc gccttctaca caccggccta aggctacacc agcgacgtaa ttgccaccca    7140
aaaatagccc ttcgtagccc gaagacgtta gagatgattt agccgtgtca aggatatcaa    7200
agtgaccaac tagaaactga ggaatggctt gaggccatac cctaactcct aatttaagtg    7260
gatcggtcga attaggctta attagcattt cctcaaatc tctgtcaact gcttccacta     7320
actcaccttc agacttggac agaattccgg tgtttgtaga cccgccaatc atgttcaaca    7380
gcaaaattct tccgggcggt gcgcgatttg gaaagagtga ggagctgtag atagttccta    7440
atgtttcaac tccttgcgtg cgtggatgca attgcccaaa acctttagt tcaccatcta     7500
tcaaacattc tgttcggatt gcttcttcg ggtacgagat agatactgct gcaactggtg     7560
ggtaatatag ttttgagagt gcatttgcag cagattcaga agagggcgc aagagaccgc     7620
ttgcaacatg agatggcacc gtcattacaa ca                                  7652
```

```
<210> SEQ ID NO 2
<211> LENGTH: 8684
<212> TYPE: DNA
<213> ORGANISM: Artificial Sequence
<220> FEATURE:
<223> OTHER INFORMATION: pEB8 (= pEB8a) plastid transformation vector
      (Example 2).

<400> SEQUENCE: 2
```

```
tttaactcga ttctatttac taatgtatca ccttcgaatt ttacttcagc tcttgtttta      60
taattaccat caccttgaa gaagattgtt ctttcttgta cgtaaccttc aggcattgct      120
gatttgaaga aatcatgttg tttcatatga tcaggatatc ttgcgaaaca ttgtactcca     180
tatccgaatg ttgatactaa tgttggccaa ggtacaggta atttacctgt tgtacagatg     240
aattttaatg ttaatttacc atatgtagca tcaccttcac cttcacctga tactgagaat    300
ttatgaccat ttacatcacc atctaattct actaagatag gtactactcc agtgaataat    360
tcttcacctt ttgaagccat gaatccctcc ctacaactat ccaggcgctt cagattcgcc    420
cggagttcgc tccagaaaat atagccatcc ctgcccctc acgtcaatcc cacgagcctc     480
ttatccattc tcattgaacg acggcgaatt cgaatagatc tacatacacc ttggttgaca    540
cgagtatata agtcatgtta tactgttgaa taacaagcct tccatttct attttgattt     600
gtagaaaact agtgtgcttg ggagtccctg atgattaaat aaaccaagat tttaccatgg    660
attgtgtgat tgtcggcgga ggtattagtg gtctttgcat cgctcaggcg cttgctacta    720
agcatcctga tgctgctccg aatttaattg tgaccgaggc taaggatcgt gttggaggca    780
acattatcac tcgtgaagag aatggttttc tctgggaaga aggtcccaat agttttcaac    840
cgtctgatcc tatgctcact atggtggtag atagtggttt gaaggatgat ttggtgttgg    900
gagatcctac tgcgccaagg tttgtgttgt ggaatgggaa attgaggccg gttccatcga    960
agctaacaga cttaccgttc tttgatttga tgagtattgg tgggaagatt agagctggtt    1020
ttggtgcact tggcattcga ccgtcacctc caggtcgtga agaatctgtg gaggagtttg    1080
tacggcgtaa cctcggtgat gaggttttg agcgcctgat tgaaccgttt tgttcaggtg     1140
tttatgctgg tgatccttca aaactgagca tgaaagcagc gtttgggaag gtttggaaac    1200
tagagcaaaa tggtggaagc ataataggtg gtacttttaa ggcaattcag gagaggaaaa    1260
```

-continued

| | | | | | |
|---|---|---|---|---|---|
| acgctcccaa | ggcagaacga | gacccgcgcc | tgccaaaacc | acagggccaa | acagttggtt | 1320 |
| ctttcaggaa | gggacttcga | atgttgccag | aagcaatatc | tgcaagatta | ggtagcaaag | 1380 |
| ttaagttgtc | ttggaagctc | ttaggtatca | ctaagctgga | gagcggagga | tacaacttaa | 1440 |
| catatgagac | tccagatggt | ttagtttccg | tgcagagcaa | aagtgttgta | atgacggtgc | 1500 |
| catctcatgt | tgcaagcggt | ctcttgcgcc | ctctttctga | atctgctgca | aatgcactct | 1560 |
| caaaactata | ttacccacca | gttgcagcag | tatctatctc | gtacccgaaa | gaagcaatcc | 1620 |
| gaacagaatg | tttgatagat | ggtgaactaa | agggttttgg | gcaattgcat | ccacgcacgc | 1680 |
| aaggagttga | aacattagga | actatctaca | gctcctcact | ctttccaaat | cgcgcaccgc | 1740 |
| ccggaagaat | tttgctgttg | aacatgattg | gcgggtctac | aaacaccgga | attctgtcca | 1800 |
| agtctgaagg | tgagttagtg | gaagcagttg | acagagattt | gaggaaaatg | ctaattaagc | 1860 |
| ctaattcgac | cgatccactt | aaattaggag | ttagggtatg | gcctcaagcc | attcctcagt | 1920 |
| ttctagttgg | tcactttgat | atccttgaca | cggctaaatc | atctctaacg | tcttcgggct | 1980 |
| acgaagggct | attttgggt | ggcaattacg | tcgctggtgt | agccttaggc | cggtgtgtag | 2040 |
| aaggcgcata | tgaaaccgcg | attgaggtca | acaacttcat | gtcacggtac | gcttacaagt | 2100 |
| aaatgtaaaa | cattaaatct | cccagactag | ttcaaccgaa | attcaattaa | ggaaataaat | 2160 |
| taaggaaata | caaaagggg | ggtagtcatt | tgtatataac | tttgtatgac | ttttctcttc | 2220 |
| tatttttttg | tatttcctcc | ctttccttt | ctatttgtat | ttttttatca | ttgcttccat | 2280 |
| tgaactgcag | aaagaaggcc | cggctccaag | ttgttcaaga | atagtggcgt | tgagtttctc | 2340 |
| gaccctttga | cttaggatta | gtcagttcta | tttctcgatg | gggcggggaa | gggatataac | 2400 |
| tcagcggtag | agtgtcacct | tgacgtggtg | gaagtcatca | gttcgagcct | gattatccct | 2460 |
| aagcccaatg | tgagtttttc | tagttggatt | tgctcccccg | ccgtcgttca | atgagaatgg | 2520 |
| ataagaggct | cgtgggattg | acgtgagggg | gcagggatgg | ctatatttct | gggagcgaac | 2580 |
| tccgggcgaa | tatgaagcgc | atggatacaa | gttatgcctt | ggaatgaaag | acaattccga | 2640 |
| atccgctttg | tctacgaaca | aggaagctat | aagtaatgca | actatgaatc | tcatggagag | 2700 |
| ttcgatcctg | gctcaggatg | aacgctggcg | gcatgcttaa | cacatgcaag | tcggacggga | 2760 |
| agtggtgttt | ccagtggcgg | acgggtgagt | aacgcgtaag | aacctgccct | tgggagggga | 2820 |
| acaacagctg | gaaacggctg | ctaatacccc | gtaggctgag | gagcaaaagg | aggaatccgc | 2880 |
| ccgaggaggg | gctcgcgtct | gattagctag | ttggtgaggc | aatagcttac | caaggcgatg | 2940 |
| atcagtagct | ggtccgagag | gatgatcagc | cacactggga | ctgagacacg | gcccagactc | 3000 |
| ctacgggagg | cagcagtggg | gaattttccg | caatgggcga | aagcctgacg | gagcaatgcc | 3060 |
| gcgtggaggt | agaaggccca | cggtcgtga | acttcttttc | ccggagaaga | agcaatgacg | 3120 |
| gtatctgggg | aataagcatc | ggctaactct | gtgccagcag | ccgcggtaat | acagaggatg | 3180 |
| caagcgttat | ccggaatgat | tgggcgcggc | ggtggagctc | cagcttttgt | tccctttagt | 3240 |
| gagggttaat | ttcgagcttg | gcgtaatcat | ggtcatagct | gtttcctgtg | tgaaattgtt | 3300 |
| atccgctcac | aattccacac | aacatacgag | ccggaagcat | aaagtgtaaa | gcctggggtg | 3360 |
| cctaatgagt | gagctaactc | acattaattg | cgttgcgctc | actgcccgct | ttccagtcgg | 3420 |
| gaaacctgtc | gtgccagctg | cattaatgaa | tcggccaacg | cgcggggaga | ggcggtttgc | 3480 |
| gtattgggcg | ctcttccgct | tcctcgctca | ctgactcgct | gcgctcggtc | gttcggctgc | 3540 |
| ggcgagcgg | atcagctcac | tcaaaggcgg | taatacggtt | atccacagaa | tcagggata | 3600 |
| acgcaggaaa | gaacatgtga | gcaaaaggcc | agcaaaaggc | caggaaccgt | aaaaaggccg | 3660 |

-continued

```
cgttgctggc gttttticcat aggctccgcc cccctgacga gcatcacaaa aatcgacgct    3720
caagtcagag gtggcgaaac ccgacaggac tataaagata ccaggcgttt ccccctggaa    3780 gctcccctcgt gcgctctcct gttccgaccc tgccgcttac cggataccctg tccgcctttc    3840 tcccttcggg aagcgtggcg ctttctcata gctcacgctg taggtatctc agttcggtgt    3900
aggtcgttcg ctccaagctg ggctgtgtgc acgaacccccc cgttcagccc gaccgctgcg    3960
ccttatccgg taactatcgt cttgagtcca acccggtaag acacgactta tcgccactgg    4020
cagcagccac tggtaacagg attagcagag cgaggtatgt aggcggtgct acagagttct    4080
tgaagtggtg gcctaactac ggctacacta aggacagt atttggtatc tgcgctctgc    4140
tgaagccagt taccttcgga aaagagttg gtagctcttg atccggcaaa caaaccaccg    4200
ctggtagcgg tggttttttt gtttgcaagc agcagattac gcgcagaaaa aaaggatctc    4260
aagaagatcc tttgatcttt tctacggggt ctgacgctca gtggaacgaa aactcacgtt    4320
aagggatttt ggtcatgaga ttatcaaaaa ggatcttcac ctagatcctt ttaaattaaa    4380
aatgaagttt taaatcaatc taaagtatat atgagtaaac ttggtctgac agttaccaat    4440
gcttaatcag tgaggcacct atctcagcga tctgtctatt tcgttcatcc atagttgcct    4500
gactccccgt cgtgtagata actacgatac gggagggctt accatctggc cccagtgctg    4560
caatgatacc gcgagaccca cgctcaccgg ctccagattt atcagcaata aaccagccag    4620
ccggaagggc cgagcgcaga agtggtcctg caactttatc cgcctccatc cagtctatta    4680
attgttgccg ggaagctaga gtaagtagtt cgccagttaa tagtttgcgc aacgttgttg    4740
ccattgctac aggcatcgtg gtgtcacgct cgtcgtttgg tatggcttca ttcagctccg    4800
gttcccaacg atcaaggcga gttacatgat cccccatgtt gtgcaaaaaa gcggttagct    4860
ccttcggtcc tccgatcgtt gtcagaagta agttggccgc agtgttatca ctcatggtta    4920
tggcagcact gcataattct cttactgtca tgccatccgt aagatgcttt tctgtgactg    4980
gtgagtactc aaccaagtca ttctgagaat agtgtatgcg gcgaccgagt tgctcttgcc    5040
cggcgtcaat acgggataat accgcgccac atagcagaac tttaaaagtg ctcatcattg    5100
gaaaacgttc ttcggggcga aaactctcaa ggatcttacc gctgttgaga tccagttcga    5160
tgtaacccac tcgtgcaccc aactgatctt cagcatcttt tactttcacc agcgtttctg    5220
ggtgagcaaa aacaggaagg caaaatgccg caaaaaaggg aataagggcg acacggaaat    5280
gttgaatact catactcttc cttttttcaat attattgaag catttatcag ggttattgtc    5340
tcatgagcgg atacatattt gaatgtattt agaaaaataa acaatagggg ttccgcgcca    5400
catttccccg aaaagtgcca cctgggaaat tgtaaacgtt aatatttgt taaaattcgc    5460 gttaaattttt tgttaaatca gctcattttt taaccaatag gccgaaatcg gcaaaatccc    5520
ttataaatca aaagaataga ccgagatagg gttgagtgtt gttccagttt ggaacaagag    5580
tccactatta agaacgtgg actccaacgt caaagggcga aaaaccgtct atcagggcga    5640
tggcccacta cgtgaaccat caccctaatc aagttttttg gggtcgaggt gccgtaaagc    5700
actaaatcgg aaccctaaag ggagcccccg atttagagct tgacgggaa agccgggttc    5760 aatggaagca atgataaaaa aatacaaata gaaaggaaa gggaggaaat acaaaaaaat    5820
agaagagaaa agtcatacaa agttatatac aaatgactac ccccctttttt gtatttcctt    5880 aatttattttc cttaattgaa tttcggttga actagtttga acgaattgtt agacattatt    5940
tgccgactac cttggtgatc tcgcctttca cgtagtggac aaattcttcc aactgatctg    6000
```

```
cgcgcgaggc caagcgatct tcttcttgtc caagataagc ctgtctagct tcaagtatga   6060
cgggctgata ctgggccggc aggcgctcca ttgcccagtc ggcagcgaca tccttcggcg   6120
cgattttgcc ggttactgcg ctgtaccaaa tgcgggacaa cgtaagcact acatttcgct   6180
catcgccagc ccagtcgggc ggcgagttcc atagcgttaa ggtttcattt agcgcctcaa   6240
atagatcctg ttcaggaacc ggatcaaaga gttcctccgc cgctggacct accaaggcaa   6300
cgctatgttc tcttgctttt gtcagcaaga tagccagatc aatgtcgatc gtggctggct   6360
cgaagatacc tgcaagaatg tcattgcgct gccattctcc aaattgcagt tcgcgcttag   6420
ctggataacg ccacggaatg atgtcgtcgt gcacaacaat ggtgacttct acagcgcgga   6480
gaatctcgct ctctccaggg gaagccgaag tttccaaaag gtcgttgatc aaagctcgcc   6540
gcgttgtttc atcaagcctt acggtcaccg taaccagcaa atcaatatca ctgtgtggct   6600
tcaggccgcc atccactgcg gagccgtaca aatgtacggc cagcaacgtc ggttcgagat   6660
ggcgctcgat gacgccaact acctctgata gttgagtcga tacttcggcg atcaccgctt   6720
ccctcatggt aaatgaaaga agaactaaa  tactatattt cactttgagg tggaaacgta   6780 acaattttttt ttattgtctt tataatattc atattggttt ttatcgtatt tattttatcc   6840
atagattata aaaattcata agaaagaca  gaatgaataa actcaaatta ttacgaatag   6900
gtctttctaa tgataaataa gtatgaattc cggcgaacgt ggcgagaaag gaagggaaga   6960
aagcgaaagg agcgggcgct agggcgctgg caagtgtagc ggtcacgctg cgcgtaacca   7020
ccacacccgc cgcgcttaat gcgccgctac agggcgcgtc gcgccattcg ccattcaggc   7080 tgccgcaactg ttgggaaggg cgatcggtgc gggcctcttc gctattacgc cagctggcga   7140 aaggggatg tgctgcaagg cgattaagtt gggtaacgcc agggttttcc cagtcacgac   7200
gttgtaaaac gacggccagt gaattgtaat acgactcact ataggggcgaa ttgggtacga   7260 aatccttccc gatacctccc aaggaaaatc tcgaatttgg atcccaaatt gacgggttag   7320
tgtgagctta tccatgcggt tatgcactct ttgaatagga atccgttttc tgaaagatcc   7380
tggctttcgt actttggtgg gtctccgaga tcctttcgat gacctatgtt gaagggatat   7440
ctatctaatc cgatcgattg cgtaaagccc gcggtagcaa cggaaccggg gaaagtatac   7500
agaaaagaca gttcttttct attatattag tattttctat tatattagat atattagact   7560
attatattag attagtatta gttagtgatc ccgacttagt gagtctgatg aattgttggc   7620
accagtccta cattttgtct ctgtggaccg aggagaaaag gggctcggcg ggaagaggag   7680
tgtaccatga gagaagcaag gaggtcaacc tcttcaaat atacaacatg gattctggca   7740
atgtagttgg actctcatgt cgatccgaat gaatcatcct ttccacggag gtaaatctt    7800 gcctgctagg caagaggata gcaagttcca aattctgtct cggtaggaca tgtatttcta   7860
ttactatgaa attcataaat gaagtagtta atggtagggt taccattatc ctttttgtag   7920
tgacgaatct tgtatgtgtt cctaagaaaa ggaatttgtc catttttcgg ggtctcaaag   7980
gggcgtggaa acgcataaga actcttgaat ggaaagaga  tgtaactcca gttccttcgg   8040
aatcggtagt caatcctatt tccgataggg gcagttgaca attgaatccg atttttgacca   8100 ttattttcat atccgtaata gtgcgactgc agaagcttct aataaaaaat atatagtaat   8160
tttttattat ttattattat tatttattat taatataata aataaagtaa aatatgatac   8220
tctataaaaa tttgctcatt tttatagaaa aaaacgagta atataagccc tctttcttat   8280
ttaaagaagg cttatattgc tcgttttttta ctaaactaga tttagactaa cactaactag   8340
acccttattt atataattca tccataccat gtgtgatacc agcagctgtt acaaattcta   8400
```

-continued

| | | | |
|---|---|---|---|
| ataataccat | atgatctctt | ttttcattag gatcttttga | taaagctgat tgtgtaccta | 8460 |
| agtaatgatt | atcaggtaat | aatacaggac catcaccgat | aggtgtattt tgttgataat | 8520 |
| gatctgctaa | ttgtactgaa | ccgtcttcga tattatgtct | gattttgaaa tttactttga | 8580 |
| taccattttt | ttgtttatca | gccatgatat atacattatg | tgaattataa ttatattcta | 8640 |
| atttatgacc | taagatatta | ccatcttctt tgaaatcgat | acct | 8684 |

<210> SEQ ID NO 3
<211> LENGTH: 10453
<212> TYPE: DNA
<213> ORGANISM: Artificial Sequence
<220> FEATURE:
<223> OTHER INFORMATION: pNY2C plastid transformation vector
       (Example 4 II).

<400> SEQUENCE: 3

| | | | | |
|---|---|---|---|---|
| ctcgagtgag | agaagaagt | gaggaatcct | cttttcgact | ctgactctcc cactccagtc | 60 |
| gttgcttttc | tttctgttac | ttcgaaagta | gctgcttcag | cttcagccac tcgaattttc | 120 |
| gatattcctt | tttatttctc | atcaaacgaa | tggcatcttc | ttctggaaat cctagctatt | 180 |
| cttagcatga | tattgggaaa | tctcattgct | attactcaaa | caagcatgaa acgtatgctt | 240 |
| gcatattcgt | ccataggcca | aatcggatat | gtaattattg | gaataattgt tggagactca | 300 |
| aatgatggat | atgcaagcat | gataacttat | atgctgttct | atatctccat gaatctagga | 360 |
| acttttgctt | gcattgtatt | atttggtcta | cgtaccggaa | ctgataacat tcgagattat | 420 |
| gcaggattat | acacaaaaga | tccttttttg | gctctctctt | tagccctatg tctcttatcc | 480 |
| ctaggaggtc | ttcctccact | agcaggtttt | ttcggaaaac | tctatttatt ctggtgtgga | 540 |
| tggcaggcag | gcctatattt | cttggtttta | ataggactcc | ttacaagcgt tgtttctatc | 600 |
| tactattatc | taaaaataat | aaagttatta | atgactggac | gaaaccaaga ataacccct | 660 |
| cacgtgcgaa | attatagaag | atccccttta | agatcaaaca | attccatcga attgagtatg | 720 |
| attgtatgtg | tgatagcatc | tactatacca | ggaatatcaa | tgaacccaat tattgcaatt | 780 |
| gctcaggata | gccttttta | gcttctaggg | tctatttctt | agttcaagat ccctcttact | 840 |
| aactggaatc | aaagaattag | tagatctgtt | ccgcccaaaa | tgggaatggg ctagggttat | 900 |
| gaacttataa | tctgatgatc | gagtcgattc | catgattata | agttcattcc ataccggacc | 960 |
| aggccggaat | agggttatat | acattctcat | tatgagaagg | ggtcattcgg gcctatctaa | 1020 |
| atagatacta | tgtttacata | gttcaatgga | agcaatgata | aaaaatca aatagaaaag | 1080 |
| gaagggagg | aaatacaaaa | aaatagaaga | gaaaagtcat | acaaagttat atacaaatga | 1140 |
| ctacccccct | ttttgtattt | ccttaattta | tttccttaat | tgaatttcgg ttgaactagt | 1200 |
| ctggagatt | taatgtttta | catttacttg | taagcgtacc | gtgacatgaa gttgttgacc | 1260 |
| tcaatcgcgg | tttcatatgc | gccttctaca | caccggccta | aggctacacc agcgacgtaa | 1320 |
| ttgccaccca | aaaatagccc | ttcgtagccc | gaagacgtta | gagatgattt agccgtgtca | 1380 |
| aggatatcaa | agtgaccaac | tagaaactga | ggaatggctt | gaggccatac cctaactcct | 1440 |
| aatttaagtg | gatcggtcga | attaggctta | attagcattt | tcctcaaatc tctgtcaact | 1500 |
| gcttccacta | actcacctc | agacttggac | agaattccgg | tgtttgtaga cccgccaatc | 1560 |
| atgttcaaca | gcaaaattct | tccgggcggt | gcgcgatttg | gaaagagtga ggagctgtag | 1620 |
| atagttccta | atgtttcaac | tccttgcgtg | cgtggatgca | attgcccaaa acccttagt | 1680 |
| tcaccatcta | tcaaacattc | tgttcggatt | gcttctttcg | ggtacgagat agatactgct | 1740 |

-continued

```
gcaactggtg ggtaatatag ttttgagagt gcatttgcag cagattcaga aagagggcgc   1800
aagagaccgc ttgcaacatg agatggcacc gtcattacaa cacttttgct ctgcacggaa   1860
actaaaccat ctggagtctc atatgttaag ttgtatcctc cgctctccag cttagtgata   1920
cctaagagct tccaagacaa cttaactttg ctacctaatc ttgcagatat tgcttctggc   1980
aacattcgaa gtcccttcct gaaagaacca actgtttggc cctgtggttt tggcaggcgc   2040
gggtctcgtt ctgccttggg agcgtttttc ctctcctgaa ttgccttaaa agtaccacct   2100
attatgcttc caccattttg ctctagtttc caaaccttcc caaacgctgc tttcatgctc   2160
agttttgaag gatcaccagc ataaacacct gaacaaaacg gttcaatcag gcgctcaaaa   2220
acctcatcac cgaggttacg ccgtacaaac tcctccacag attcttcacg acctggaggt   2280
gacggtcgaa tgccaagtgc accaaaacca gctctaatct tcccaccaat actcatcaaa   2340
tcaaagaacg gtaagtctgt tagcttcgat ggaaccggcc tcaatttccc attccacaac   2400
acaaaccttg gcgcagtagg atctcccaac accaaatcat ccttcaaacc actatctacc   2460
accatagtga gcataggatc agacggttga aaactattgg gaccttcttc ccagagaaaa   2520
ccattctctt cacgagtgat aatgttgcct ccaacacgat ccttagcctc ggtcacaatt   2580
aaattcggag cagcatcagg atgcttagta gcaagcgcct gagcgatgca aagaccacta   2640
atacctccgc cgacaatcac acaatccatg aatccctccc tacaactgat tcggaattgt   2700
cttctccttcc aaggataact tgtatccagg cgcttcagat tattagcctg gagttcgcca   2760
ccagcagtat agccaaccct accctatcac gtcaatccca caagcctctt atccattccc   2820
gttcgatcgt ggtgaattag cttctatgga ttcctacatc attacattcc atttaggatt   2880
aggaatacgc gtaatcggac ctgcttttta catatctcta ttgggaccct attcacctct   2940
ttgagtgaat cgagaaatag gtttgattgt ccatcttttt gatatatatc aggcattgca   3000
ttctccggat aattcaaatc gaagcaattg gatgtccaac tcgggcctat atgacatgac   3060
cgatcaatag atccaccttt gtcatatatt ccatacatca cactagatag atatcatatt   3120
catgaaatac gattcacttt caagatgcct tggtggtgaa atggtagaca cgcgagactc   3180
aaaatctcgt gctaaatagc gtggaggttc gagtcctctt caaggcataa tattgagaat   3240
gctcattgaa tgagcattct caataagaga gctcggatcg aatcggtatt gatataccga   3300
ttcgatccga gctcttggaa ttggaataaa ttcggcagcg gatcgcgaaa tcttggtgat   3360
cttctctatc taatgaatgg ggagtccgct ttaaaatcgt ccgccctgca cccacccccc   3420
gagtatatgc ttcaacagga atcacacaag ggtagattag aaacctctgg taaaatgccc   3480
gcccgtaacc cagcagataa agtacattac atagtccagg gattggcgac ttacccattc   3540
agtgactttg gcactggacg ttcccaaaat ggggactatc gggtaaattc aatataatag   3600
acgcctgttg gcattccagc cttccttctc ctttcagggc ctatccgaaa gagaatccag   3660
tacttcttgg tcgtgaatat ctgaactggt tgtttgctgt tcaagaattc ttgtttaggc   3720
agttcatacc atccatacat agtgttttga tctaagattt caattcttcc gtgtttcagc   3780
agtaacatat tcttccatgg agctaaggtc caaaatatgg aagaaacaag cgtttccacg   3840
actctaccac ccagtcaatt ctgttccact taatccctct ttcatggcca catatctttc   3900
cggctaagga atgggaaatc tttctcctgt tacatgaatc caattttcat ttcatccggg   3960
aaaagccatc ttttctcaa caatgtcttt gtcatttgat ccaatagcgt tccgttagat   4020
aggaacagat ttgataaata ctgataactc tcggatagag tattagaacg gaaagatcca   4080
```

-continued

```
ttagataatg aactgttggt tctaagccat ctctgacgat taatcaacaa ttcgaagtgc    4140
ttttcttgcg tattcttgat aaaccagcgt ttatatatag atgtaggagg gtctgtttgg    4200
gaagtaagaa gcccctttga catctcttca tctgcaaata attctcgatg tgaaaacaca    4260
gagccagggg gctgatcttt gaataggaaa aagagtggat caattcgaat agatctacat    4320
acaccttggt tgacacgagt atataagtca tgttatactg ttgaataaca agccttccat    4380
tttctatttt gatttgtaga aaactagtgt gcttgggagt ccctgatgat taaataaacc    4440
aagattttac catgagggaa gcggtgatcg ccgaagtatc gactcaacta tcagaggtag    4500
ttggcgtcat cgagcgccat ctcgaaccga cgttgctggc cgtacatttg tacggctccg    4560
cagtggatgg cggcctgaag ccacacagtg atattgattt gctggttacg gtgaccgtaa    4620
ggcttgatga aacaacgcgg cgagctttga tcaacgacct tttggaaact tcggcttccc    4680
ctggagagag cgagattctc cgcgctgtag aagtcaccat tgttgtgcac gacgacatca    4740
ttccgtggcg ttatccagct aagcgcgaac tgcaatttgg agaatggcag cgcaatgaca    4800
ttcttgcagg tatcttcgag ccagccacga tcgacattga tctggctatc ttgctgacaa    4860
aagcaagaga acatagcgtt gccttggtag gtccagcggc ggaggaactc tttgatccgg    4920
ttcctgaaca ggatctattt gaggcgctaa atgaaacctt aacgctatgg aactcgccgc    4980
ccgactgggc tggcgatgag cgaaatgtag tgcttacgtt gtcccgcatt tggtacagcg    5040
cagtaaccgg caaaatcgcg ccgaaggatg tcgctgccga ctgggcaatg gagcgcctgc    5100
cggcccagta tcagcccgtc atacttgaag ctagacaggc ttatcttgga caagaagaag    5160
atcgcttggc ctcgcgcgca gatcagttgg aagaatttgt ccactacgtg aaaggcgaga    5220
tcaccaaggt agtcggcaaa taatgtctaa caattcgttc aaactagaac tagttagtgt    5280
tagtctaaat ctagtttagt aaaaaacgag caatataagc cttctttaaa taagaaagag    5340
ggcttatatt actcgttttt ttctataaaa atgagcaaat ttttatagag tatcatatt t    5400 tactttattt attatattaa taataaataa taataataaa taataaaaaa ttactatata    5460 tttttttatta gaagctgggt cccaaatgaa ttggcttatt cgaaaaaggc cttgttcttt    5520
ggaagatcta tctcgtgtct ggtactgcat ggttccactc tgcaagaact ccgaatcatt    5580
ctcttgaagc tcatcctctt catcataaat gatccgcttg ccccgaaatg acctggacca    5640 ataggggaaat cccaattcat tgggcctttc gatacaatca aatagaaagc cccaagggcg    5700
ccatattcta ggagcccaaa ctatgtgatt gaataaatcc tcctgcggt caagggctcc    5760 ttctccctcc ccttcttcaa actccgattc atattttca tagagaaatc tctgatcaag    5820
gatagaacaa gagccgtttt gcatcatatc taagggattc ctcggttcgg gccgaagaag    5880
caatgtcact cgatcattat caaactgact gcaatctttt tctgtccgtg aagatcccac    5940
cagagcgcct tctacttcta ataggccatg aactagatca gaatcattct caacgagtcc    6000
ataagaagtg atcccatttt tttcatcggg tccggtaaaa gaccaaagat cttgagcgac    6060
cgatccggca gaacaactca aaagataaag aagtatcgtt aatctcttca tgctcgttcc    6120
aagctcgaag taccatttgt acaaataaga atccccttcg ttcatgatt tcttcttcat    6180 atagatagat ataggatcta tgggcaatt acttagaagt acattttgtg ctacagccct    6240
tcctatctga tagaaaagga tcccatgatc ctgaaccgat cttacctggg atcgcaaatc    6300
ccaagtttgt ctatgaagag cggatctaat tgtattagtg tctataattg atttcttctg    6360
tgtaatacta atcgatagga cctcattggt aagtgctaca agatctcgtg cattggaacc    6420
catggttatg gacccgaatc cgttagtatg gaacattttc ttttccaagt gaaatcccct    6480
```

```
agtatatgaa agagtgaaaa agtgctttcg ttgttgtgga agaagaagcc ttcgtatctt    6540
aatgcacgta tttaatttat tcggagctat tagagcggga tccactttt ggggaatatg     6600
agtcgaagca ataacaagaa tatttctagt agaacatctt tcacaatccc tggagagatg    6660
gttcactaat agaccgaggg ctaagtcatt cgactcattc acatccagat catgaatgtt    6720
tggaatccat attatgcaag gagacattgc ttttgctaat tcgaattgaa gggtgatata    6780
aaatcggtct atttccggca tcatatccat agttagccca ttcatcctag ttagcagttt    6840
cagctccgta tcaaggtcac gatcgatatc gtcactagca tcaagattgt cactatcatc    6900
aatatcgtca ctatcatcaa tatcgatctc atcaagaaga aaacctttag gcttgttatc    6960
caggaacttg ttcagaaata ccgtaatgaa aggaacatag gagtttgtcg ctaggtattt    7020
gaccaaatag gatcgtccag ttcctataga acctatcact aaaataccc tagaggggga     7080
taaggctaag cggagcgaaa agggttttcc atgagatggg aaatgaaaac tattttcccc    7140
acacgaagtt tgtgaataag tgattgtctg ataatgagca aggaatatcc gtctttctgc    7200
taaacaggat ggattgaact cataattcat tagatgcttt ttatgaatgt caactaagta    7260
tcgtaagtaa attgctcccg gttgttcaat catttgataa ccagagtcat tctttgataa    7320
acgatcacta tgagtcagac tcaatagaat ttgatcaatc ctattttctg tcgttaaggt    7380
ggagaactga accaagaatt ctctttcttc atcatcaatc gaatcactgt tcgcgaccca    7440
ggattctatt ttatcatcaa tccaatcccc gttcacgttt tttctttttc ttatcaatga    7500
atagatctct ttacttgtat gacttagatg tctcgtattt ctcgaaaaag tgattcgatt    7560
gatgggattt ggtatgagat cgatgatctc gatgagattg atattccaat ctttcttctt    7620
agaacgtatt gatttgaccc cataagcggg accaagcatg ttgccgccag aagcagaacc    7680
ccgtatttct tctagatacc taggtgagct ctggtaccct ctagtcaagg ccttaagtga    7740
gtcgtattac ggactggccg tcgttttaca acgtcgtgac tgggaaaacc ctggcgttac    7800
ccaacttaat cgccttgcag cacatccccc tttcgccagc tggcgtaata gcgaagaggc    7860
ccgcaccgat cgcccttccc aacagttgcg cagcctgaat ggcgaatggc gcttcgcttg    7920
gtaataaagc ccgcttcggc gggctttttt ttgttaacta cgtcaggtgg cacttttcgg    7980
ggaaatgtgc gcggaacccc tatttgttta ttttctaaa tacattcaaa tatgtatccg     8040
ctcatgagac aataaccctg ataaatgctt caataatatt gaaaaggaa gagtatgagt     8100
attcaacatt tccgtgtcgc ccttattccc ttttttgcgg catttgcct tcctgttttt     8160
gctcacccag aaacgctggt gaaagtaaaa gatgctgaag atcagttggg tgcacgagtg    8220
ggttacatcg aactggatct caacagcggt aagatcctg agagtttcg ccccgaagaa      8280
cgttctccaa tgatgagcac ttttaaagtt ctgctatgtg gcgcggtatt atcccgtgtt    8340
gacgccgggc aagagcaact cggtcgccgc atacactatt ctcagaatga cttggttgag    8400
tactcaccag tcacagaaaa gcatcttacg gatggcatga cagtaagaga attatgcagt    8460
gctgccataa ccatgagtga taacactgcg gccaacttac ttctgacaac gatcggagga    8520
ccgaaggagc taaccgcttt tttgcacaac atggggatc atgtaactcg ccttgatcgt     8580
tgggaaccgg agctgaatga agccatacca aacgacgagc gtgacaccac gatgcctgta    8640
gcaatggcaa caacgttgcg caaactatta actggcgaac tacttactct agcttcccgg    8700
caacaattaa tagactggat ggaggcggat aaagttgcag gaccacttct gcgctcggcc    8760
cttccggctg gctggtttat tgctgataaa tctggagccg gtgagcgtgg gtctcgcggt    8820
```

```
atcattgcag cactgggggcc agatggtaag ccctcccgta tcgtagttat ctacacgacg    8880
gggagtcagg caactatgga tgaacgaaat agacagatcg ctgagatagg tgcctcactg    8940
attaagcatt ggtaactgtc agaccaagtt tactcatata tactttagat tgatttaccc    9000
cggttgataa tcagaaaagc cccaaaaaca ggaagattgt ataagcaaat atttaaattg    9060
taaacgttaa tattttgtta aaattcgcgt taaattttg ttaaatcagc tcatttttta    9120
accaataggc cgaaatcggc aaaatccctt ataaatcaaa agaatagccc gagatagggt    9180
tgagtgttgt tccagtttgg aacaagagtc cactattaaa gaacgtggac tccaacgtca    9240
aagggcgaaa aaccgtctat cagggcgatg gcccactacg tgaaccatca cccaaatcaa    9300
gttttttggg gtcgaggtgc cgtaaagcac taaatcggaa ccctaaaggg agcccccgat    9360
ttagagcttg acgggaaag cgaacgtggc gagaaaggaa gggaagaaag cgaaaggagc    9420
gggcgctagg gcgctggcaa gtgtagcggt cacgctgcgc gtaaccacca cacccgccgc    9480
gcttaatgcg ccgctacagg gcgcgtaaaa ggatctaggt gaagatcctt tttgataatc    9540
tcatgaccaa aatcccttaa cgtgagtttt cgttccactg agcgtcagac cccgtagaaa    9600
agatcaaagg atcttcttga gatccttttt ttctgcgcgt aatctgctgc ttgcaaacaa    9660
aaaaaccacc gctaccagcg gtggtttgtt tgccggatca agagctacca actctttttc    9720
cgaaggtaac tggcttcagc agagcgcaga taccaaatac tgttcttcta gtgtagccgt    9780
agttaggcca ccacttcaag aactctgtag caccgcctac atacctcgct ctgctaatcc    9840
tgttaccagt ggctgctgcc agtggcgata agtcgtgtct taccgggttg gactcaagac    9900
gatagttacc ggataaggcg cagcggtcgg gctgaacggg gggttcgtgc acacagccca    9960
gcttggagcg aacgacctac accgaactga gatacctaca gcgtgagcta tgagaaagcg    10020
ccacgcttcc cgaagggaga aaggcggaca ggtatccggt aagcggcagg gtcggaacag    10080
gagagcgcac gagggagctt ccaggggaa acgcctggta tctttatagt cctgtcgggt    10140
ttcgccacct ctgacttgag cgtcgatttt tgtgatgctc gtcaggggg cggagcctat    10200 ggaaaaacgc cagcaacgcg gccttttac ggttcctggc cttttgctgg ccttttgctc    10260
acatgtaatg tgagttagct cactcattag gcaccccagg ctttacactt tatgcttccg    10320
gctcgtatgt tgtgtggaat tgtgagcgga taacaatttc acacaggaaa cagctatgac    10380
catgattacg ccaagctacg taatacgact cactagtggg cagatcttcg aatgcatcgc    10440
gcgcaccgta cgt                                                       10453
```

<210> SEQ ID NO 4
<211> LENGTH: 173
<212> TYPE: DNA
<213> ORGANISM: Artificial Sequence
<220> FEATURE:
<223> OTHER INFORMATION: DNA sequence of the maize plastid 16S PEP-NEP
     rRNA gene promoter
     fused to the N. tabacum plastid rbcL ribosome binding site (RBS).

<400> SEQUENCE: 4

```
gaattcacca cgatcgaacg ggaatggata agaggcttgt gggattgacg tgatagggta     60
gggttggcta tactgctggt ggcgaactcc aggctaataa tctgaagcgc ctggatacaa    120
gttatccttg gaaggaaaga caattccgaa tcagttgtag ggagggattc atg           173
```

<210> SEQ ID NO 5
<211> LENGTH: 34
<212> TYPE: DNA
<213> ORGANISM: Artificial Sequence

```
<220> FEATURE:
<223> OTHER INFORMATION: Top primer for amplification of the 16S PEP-NEP
      rRNA gene promote
      r from maize plastid DNA, the primer comprising an EcoRI restrict
      ion site (Example 1 I).

<400> SEQUENCE: 5
gccagaattc accacgatcg aacgggaatg gata                                 34

<210> SEQ ID NO 6
<211> LENGTH: 77
<212> TYPE: DNA
<213> ORGANISM: Artificial Sequence
<220> FEATURE:
<223> OTHER INFORMATION: Bottom primer comprising a BspHI restriction
      site (Example 1 I).

<400> SEQUENCE: 6
gccgtcatga atccctccct acaactgatt cggaattgtc tttccttcca aggataactt     60
gtatccaggc gcttcag                                                    77

<210> SEQ ID NO 7
<211> LENGTH: 20
<212> TYPE: DNA
<213> ORGANISM: Artificial Sequence
<220> FEATURE:
<223> OTHER INFORMATION: Top primer for amplification of the A. thaliana
      ppo gene (Example
      1 II).

<400> SEQUENCE: 7
ccacgcacgc aaggagttga                                                 20

<210> SEQ ID NO 8
<211> LENGTH: 27
<212> TYPE: DNA
<213> ORGANISM: Artificial Sequence
<220> FEATURE:
<223> OTHER INFORMATION: Bottom primer for amplification of the A.
      thaliana ppo gene, the
      primer comprising a SpeI restriction site (Example 1 II).

<400> SEQUENCE: 8
cggtactagt ctgggagatt taatgtt                                         27

<210> SEQ ID NO 9
<211> LENGTH: 25
<212> TYPE: DNA
<213> ORGANISM: Artificial Sequence
<220> FEATURE:
<223> OTHER INFORMATION: Top strand primer for amplification of the N.
      tabacum psbA gene p
      romoter, the primer comprising an EcoRI restriction site (Example
      1 III).

<400> SEQUENCE: 9
ttaagaattc gaatagatct acata                                           25

<210> SEQ ID NO 10
<211> LENGTH: 22
<212> TYPE: DNA
<213> ORGANISM: Artificial Sequence
<220> FEATURE:
<223> OTHER INFORMATION: Bottom strand primer for amplification of
      the N. tabacum psbA gen
      e promoter, the primer comprising a NcoI restriction site (Exampl
      e 1 III).
```

-continued

```
<400> SEQUENCE: 10
cagccatggt aaaatcttgg tt                                              22

<210> SEQ ID NO 11
<211> LENGTH: 30
<212> TYPE: DNA
<213> ORGANISM: Artificial Sequence
<220> FEATURE:
<223> OTHER INFORMATION: Top primer for amplification of the A. thaliana
      clpP gene promote
      r, the primer comprising an EcoRI restriction site (Example 1 V).

<400> SEQUENCE: 11
gcggaattca tcattcagaa gcccgttcgt                                      30

<210> SEQ ID NO 12
<211> LENGTH: 28
<212> TYPE: DNA
<213> ORGANISM: Artificial Sequence
<220> FEATURE:
<223> OTHER INFORMATION: Bottom primer for amplification of the A.
      thaliana clpP gene prom
      oter, the primer comprising a BspHI restriction site (Example 1 V
      ).

<400> SEQUENCE: 12
gcgtcatgaa atgaaagaaa aagagaat                                        28

<210> SEQ ID NO 13
<211> LENGTH: 33
<212> TYPE: DNA
<213> ORGANISM: Artificial Sequence
<220> FEATURE:
<223> OTHER INFORMATION: Top primer for amplification of a new plastid
      DNA target locus, t
      he primer comprising an XhoI restriction site (Example 4 I).

<400> SEQUENCE: 13
agttatctcg agtgagagaa agaagtgagg aat                                  33

<210> SEQ ID NO 14
<211> LENGTH: 21
<212> TYPE: DNA
<213> ORGANISM: Artificial Sequence
<220> FEATURE:
<223> OTHER INFORMATION: Bottom primer for amplification of a new
      plastid DNA target locus
      , the primer comprising an XbaI restriction site (Example 4 I).

<400> SEQUENCE: 14
ttctctagaa gaaatacggg g                                               21

<210> SEQ ID NO 15
<211> LENGTH: 79
<212> TYPE: DNA
<213> ORGANISM: staphylococcus aureaus bacteriophage X2

<400> SEQUENCE: 15
gttaaagaat gtagctgact gcatacttaa accacccata ctagttgctg ggtggttttt     60
atgttataat ataaatgtg                                                  79

<210> SEQ ID NO 16
<211> LENGTH: 110
<212> TYPE: DNA
<213> ORGANISM: Kluyvera Bacteriophage kvp1
```

-continued

```
<400> SEQUENCE: 16
tctagagaca ttacgttctc cccttgagtg atacacaatg agaaccaact cgtttcaagt     60
agtacctcac ataacttatc ttttaaatca acagaaggag attcaccatg               110

<210> SEQ ID NO 17
<211> LENGTH: 97
<212> TYPE: DNA
<213> ORGANISM: Bacteriophage T3

<400> SEQUENCE: 17
tctagaggga gacctcatct ttgaaatgag cgatgactaa aggttggagt cctttggttt     60 cccttatct ttaataactt aggagattta attcatg                              97

<210> SEQ ID NO 18
<211> LENGTH: 194
<212> TYPE: DNA
<213> ORGANISM: artificial sequence
<220> FEATURE:
<223> OTHER INFORMATION: chimeric X2 promoter and kvpi gene 10 5;UTP
<220> FEATURE:
<221> NAME/KEY: misc_feature
<222> LOCATION: (1)..(194)

<400> SEQUENCE: 18
aattcgttaa agaatgtagc tgactgcata cttaaaccac ccatactagt tgctgggtgg     60
tttttatgtt ataatataaa tgtgtctaga gacattacgt tctcccttg agtgatacac     120 aatgagaacc aactcgtttc aagtagtacc tcacataact tatcttttaa atcaacagaa    180
ggagattcac catg                                                      194

<210> SEQ ID NO 19
<211> LENGTH: 10011
<212> TYPE: DNA
<213> ORGANISM: artificial sequence
<220> FEATURE:
<223> OTHER INFORMATION: plasmid pEB10

<400> SEQUENCE: 19
agcttctaat aaaaaatata tagtaatttt ttattattta ttattattat ttattattaa     60
tataataaat aaagtaaaat atgatactct ataaaaattt gctcattttt atagaaaaaa    120
acgagtaata taagccctct ttcttattta agaaggctt atattgctcg ttttttacta     180
aactagattt agactaacac taactagttc tagagcaatt cccgaggctg tagccgacga    240
tggtgcgcca ggagagttgt tgattcattg tttgcctccc tgctgcggtt tttcaccgaa    300
gttcatgcca gtccagcgtt tttgcagcag aaaagccgcc gacttcggtt tgcggtcgcg    360
agtgaagatc cctttcttgt taccgccaac gcgcaatatg ccttgcgagg tcgcaaaatc    420
ggcgaaattc catacctgtt caccgacgac ggcgctgacg cgatcaaaga cgcggtgata    480
catatccagc catgcacact gatactcttc actccacatg tcggtgtaca ttgagtgcag    540
cccggctaac gtatccacgc cgtattcggt gatgataatc ggctgatgca gtttctcctg    600
ccaggccaga agttcttttt ccagtacctt ctctgccgtt tccaaatcgc cgctttggac    660
ataccatccg taataacggt tcaggcacag cacatcaaag agatcgctga tggtatcggt    720
gtgagcgtcg cagaacatta cattgacgca ggtgatcgga cgcgtcgggt cgagtttacg    780
cgttgcttcc gccagtggcg cgaaatattc ccgtgcacct tgcggacggg tatccggttc    840
gttggcaata ctccacatca ccacgcttgg gtggttttg tcacgcgcta tcagctcttt    900
```

```
aatcgcctgt aagtgcgctt gctgagtttc cccgttgact gcctcttcgc tgtacagttc    960
tttcggcttg ttgcccgctt cgaaaccaat gcctaaagag aggttaaagc cgacagcagc   1020
agtttcatca atcaccacga tgccatgttc atctgcccag tcgagcatct cttcagcgta   1080
agggtaatgc gaggtacggt aggagttggc cccaatccaa tccattaatg cgtggtcgtg   1140
caccatcagc acgttatcga atcctttgcc acgcaagtcc gcatcttcat gacgaccaaa   1200
gccagtaaag tagaacggtt tgtggttaat caggaactgt tcgcccttca ctgccactga   1260
ccggatgccg acgcgaagcg ggtagatatc acactctgtc tggcttttgg ctgtgacgca   1320
cagttcatag agataacctt cacccggttg ccagaggtgc ggattcacca cttgcaaagt   1380
cccgctagtg ccttgtccag ttgcaaccac ctgttgatcc gcatcacgca gttcaacgct   1440
gacatcacca ttggccacca cctgccagtc aacagacgcg tggttacagt cttgcgcgac   1500
atgcgtcacc acggtgatat cgtccaccca ggtgttcggc gtggtgtaga gcattacgct   1560
gcgatggatc ccggcatagt taaagaaatc atggaagtaa gactgctttt tcttgccgtt   1620
ttcgtcggta atcaccattc ccggcgggat agtctgccag ttcagttcgt tgttcacaca   1680
aacggtgata cgtacacttt tcccggcaat aacatacggc gtgacatcgg cttcaaatgg   1740
cgtatagccg ccctgatgct ccatcacttc ctgattattg acccacactt tgccgtaatg   1800
agtgaccgca tcgaaacgca gcacgatacg ctggcctgcc caacctttcg gtataaagac   1860
ttcgcgctga taccagacgt tgcccgcata attacgaata tctgcatcgg cgaactgatc   1920
gttaaaactg cctggcacag caattgcccg gctttcttgt aacgcgcttt cccaccaacg   1980
ctgatcaatt ccacagtttt cgcgatccag actgaatgcc cacaggccgt cgagtttttt   2040
gatttcacgg gttggggttt ctacaggacg gaccatggat taaatctcct aagttattaa   2100
agataaaggg aaaccaaagg actccaacct ttagtcatcg ctcatttcaa agatgaggtc   2160
tccctctacc cgggaagaga ttcggaattg tctttccttc caaggataac ttgtatccag   2220
gcgcttcaga ttattagcct ggagttcgcc accagcagta tagccaaccc taccctatca   2280
cgtcaatccc acaagcctct tatccattcc cgttcgatcg tggtgaattc gaatagatct   2340
attcgaattc gttaaagaat gtagctgact gcatacttaa accacccata ctagttgctg   2400
ggtggttttt atgttataat ataaatgtgt ctagagacat tacgttctcc ccttgagtga   2460
tacacaatga gaaccaactc gtttcaagta gtacctcaca taacttatct tttaaatcaa   2520
cagaaggaga ttcaccatgg attgtgtgat tgtcggcgga ggtattagtg gtctttgcat   2580
cgctcaggcg cttgctacta agcatcctga tgctgctccg aatttaattg tgaccgaggc   2640
taaggatcgt gttggaggca acattatcac tcgtgaagag aatggttttc tctgggaaga   2700
ggtcccaat agttttcaac cgtctgatcc tatgctcact atggtggtag atagtggttt   2760
gaaggatgat ttggtgttgg gagatcctac tgcgccaagg tttgtgttgt ggaatgggaa   2820
attgaggccg gttccatcga agctaacaga cttaccgttc tttgatttga tgagtattgg   2880
tgggaagatt agagctggtt ttggtgcact tggcattcga ccgtcacctc caggtcgtga   2940
agaatctgtg gaggagtttg tacggcgtaa cctcggtgat gaggttttttg agcgcctgat   3000
tgaaccgttt tgttcaggtg tttatgctgg tgatccttca aaactgagca tgaaagcagc   3060
gtttgggaag gtttggaaac tagagcaaaa tggtggaagc ataataggtg gtacttttaa   3120
ggcaattcag gagaggaaaa acgctcccaa ggcagaacga gacccgcgcc tgccaaaacc   3180
acagggccaa acagttggtt cttttcaggaa gggacttcga atgttgccag aagcaatatc   3240
tgcaagatta ggtagcaaag ttaagttgtc cttggaagctc ttaggtatca ctaagctgga   3300
```

```
gagcggagga tacaacttaa catatgagac tccagatggt ttagtttccg tgcagagcaa   3360
aagtgttgta atgacggtgc catctcatgt tgcaagcggt ctcttgcgcc ctctttctga   3420
atctgctgca aatgcactct caaaactata ttacccacca gttgcagcag tatctatctc   3480
gtacccgaaa gaagcaatcc gaacagaatg tttgatagat ggtgaactaa agggttttgg   3540
gcaattgcat ccacgcacgc aaggagttga acattagga actatctaca gctcctcact   3600
cttttccaaat cgcgcaccgc ccggaagaat tttgctgttg aacatgattg gcgggtctac   3660
aaacaccgga attctgtcca agtctgaagg tgagttagtg gaagcagttg acagagattt   3720
gaggaaaatg ctaattaagc ctaattcgac cgatccactt aaattaggag ttagggtatg   3780
gcctcaagcc attcctcagt ttctagttgg tcactttgat atccttgaca cggctaaatc   3840
atctctaacg tcttcgggct acgaagggct attttttgggt ggcaattacg tcgctggtgt   3900
agccttaggc cggtgtgtag aaggcgcata tgaaaccgcg attgaggtca acaacttcat   3960
gtcacggtac gcttacaagt aaatgtaaaa cattaaatct cccagactag ttcaaccgaa   4020
attcaattaa ggaaataaat taaggaaata caaaaagggg ggtagtcatt tgtatataac   4080
tttgtatgac ttttctcttc tattttttg tatttcctcc ctttccttt ctatttgtat    4140
tttttttatca ttgcttccat tgaactgcag aaagaaggcc cggctccaag ttgttcaaga   4200
atagtggcgt tgagtttctc gacccttga cttaggatta gtcagttcta tttctcgatg    4260
gggcggggaa gggatataac tcagcggtag agtgtcacct tgacgtggtg gaagtcatca   4320
gttcgagcct gattatccct aagcccaatg tgagtttttc tagttggatt tgctcccccg   4380
ccgtcgttca atgagaatgg ataagaggct cgtgggattg acgtgagggg gcagggatgg   4440
ctatatttct gggagcgaac tccgggcgaa tatgaagcgc atggatacaa gttatgcctt   4500
ggaatgaaag acaattccga atccgctttg tctacgaaca aggaagctat aagtaatgca   4560
actatgaatc tcatggagag ttcgatcctg gctcaggatg aacgctggcg gcatgcttaa   4620
cacatgcaag tcggacggga agtggtgttt ccagtggcgg acgggtgagt aacgcgtaag   4680
aacctgccct tgggagggga acaacagctg gaaacggctg ctaataccc gtaggctgag    4740
gagcaaaagg aggaatccgc ccgaggaggg gctcgcgtct gattagctag ttggtgaggc   4800
aatagcttac caaggcgatg atcagtagct ggtccgagag gatgatcagc cacactggga   4860
ctgagacacg gcccagactc ctacgggagg cagcagtggg gaattttccg caatgggcga   4920
aagcctgacg gagcaatgcc gcgtggaggt agaaggccca cgggtcgtga acttcttttc   4980
ccggagaaga agcaatgacg gtatctgggg aataagcatc ggctaactct gtgccagcag   5040
ccgcggtaat acagaggatg caagcgttat ccggaatgat tgggcgcggc ggtggagctc   5100
cagcttttgt tccctttagt gagggttaat ttcgagcttg gcgtaatcat ggtcatagct   5160
gtttcctgtg tgaaattgtt atccgctcac aattccacac aacatacgag ccggaagcat   5220
aaagtgtaaa gcctggggtg cctaatgagt gagctaactc acattaattg cgttgcgctc   5280
actgcccgct ttccagtcgg gaaacctgtc gtgccagctg cattaatgaa tcggccaacg   5340
cgcgggaga ggcggtttgc gtattgggcg ctcttccgct tcctcgctca ctgactcgct    5400
gcgctcggtc gttcggctgc ggcgagcggt atcagctcac tcaaaggcgg taatacggtt   5460
atccacagaa tcagggata acgcaggaaa gaacatgtga gcaaaaggcc agcaaaaggc    5520
caggaaccgt aaaaaggccg cgttgctggc gtttttccat aggctccgcc cccctgacga   5580
gcatcacaaa aatcgacgct caagtcagag gtggcgaaac ccgacaggac tataaagata   5640
```

```
ccaggcgttt cccctggaa gctccctcgt gcgctctcct gttccgaccc tgccgcttac    5700
cggatacctg tccgccttc tcccttcggg aagcgtggcg ctttctcata gctcacgctg    5760
taggtatctc agttcggtgt aggtcgttcg ctccaagctg ggctgtgtgc acgaaccccc    5820
cgttcagccc gaccgctgcg ccttatccgg taactatcgt cttgagtcca acccggtaag    5880
acacgactta tcgccactgg cagcagccac tggtaacagg attagcagag cgaggtatgt    5940
aggcggtgct acagagttct tgaagtggtg gcctaactac ggctacacta aaggacagt    6000 atttggtatc tgcgctctgc tgaagccagt taccttcgga aaagagttg gtagctcttg    6060 atccggcaaa caaccaccg ctggtagcgg tggtttttt gtttgcaagc agcagattac    6120
gcgcagaaaa aaggatctc aagaagatcc tttgatcttt tctacggggt ctgacgctca    6180
gtggaacgaa aactcacgtt aagggattt ggtcatgaga ttatcaaaaa ggatcttcac    6240
ctagatcctt ttaaattaaa aatgaagttt taaatcaatc taaagtatat atgagtaaac    6300
ttggtctgac agttaccaat gcttaatcag tgaggcacct atctcagcga tctgtctatt    6360
tcgttcatcc atagttgcct gactccccgt cgtgtagata actacgatac gggagggctt    6420
accatctggc cccagtgctg caatgatacc gcgagaccca cgctcaccgg ctccagattt    6480
atcagcaata aaccagccag ccggaagggc cgagcgcaga agtggtcctg caactttatc    6540
cgcctccatc cagtctatta ttgttgccg ggaagctaga gtaagtagtt cgccagttaa    6600
tagtttgcgc aacgttgttg ccattgctac aggcatcgtg gtgtcacgct cgtcgtttgg    6660
tatggcttca ttcagctccg gttcccaacg atcaaggcga gttacatgat cccccatgtt    6720
gtgcaaaaaa gcggttagct ccttcggtcc tccgatcgtt gtcagaagta agttggccgc    6780
agtgttatca ctcatggtta tggcagcact gcataattct cttactgtca tgccatccgt    6840
aagatgcttt tctgtgactg gtgagtactc aaccaagtca ttctgagaat agtgtatgcg    6900
gcgaccgagt tgctcttgcc cggcgtcaat acgggataat accgcgccac atagcagaac    6960
tttaaaagtg ctcatcattg gaaaacgttc ttcggggcga aaactctcaa ggatcttacc    7020
gctgttgaga tccagttcga tgtaacccac tcgtgcaccc aactgatctt cagcatcttt    7080
tactttcacc agcgtttctg ggtgagcaaa aacaggaagg caaaatgccg caaaaaaggg    7140
aataagggcg acacggaaat gttgaatact catactcttc ctttttcaat attattgaag    7200
catttatcag ggttattgtc tcatgagcgg atacatattt gaatgtattt agaaaaataa    7260
acaaataggg gttccgcgca catttccccg aaaagtgcca cctggaaat tgtaaacgtt    7320 aatattttgt taaaattcgc gttaaatttt tgttaaatca gctcattttt taaccaatag    7380
gccgaaatcg gcaaaatccc ttataaatca aagaataga ccgagatagg gttgagtgtt    7440
gttccagttt ggaacaagag tccactatta agaacgtgg actccaacgt caagggcga    7500 aaaccgtct atcagggcga tggcccacta cgtgaaccat caccctaatc aagttttttg    7560
gggtcgaggt gccgtaaagc actaaatcgg aaccctaaag ggagccccg atttagagct    7620 tgacggggaa agccggttca atggaagcaa tgataaaaaa atacaaatag aaaaggaaag    7680
ggaggaaata caaaaaata gaagagaaaa gtcatacaaa gttatataca aatgactacc    7740
cccctttttg tatttcctta atttattcc ttaattgaat ttcggttgaa ctagtttgaa    7800
cgaattgtta gacattattt gccgactacc ttggtgatct cgcctttcac gtagtggaca    7860
aattcttcca actgatctgc gcgcgaggcc aagcgatctt cttcttgtcc aagataagcc    7920
tgtctagctt caagtatgac gggctgatac tgggccggca ggcgctccat tgcccagtcg    7980
gcagcgacat ccttcggcgc gattttgccg gttactgcgc tgtaccaaat gcgggacaac    8040
```

-continued

```
gtaagcacta catttcgctc atcgccagcc cagtcgggcg gcgagttcca tagcgttaag      8100
gtttcattta gcgcctcaaa tagatcctgt tcaggaaccg gatcaaagag ttcctccgcc      8160
gctggaccta ccaaggcaac gctatgttct cttgcttttg tcagcaagat agccagatca      8220
atgtcgatcg tggctggctc gaagatacct gcaagaatgt cattgcgctg ccattctcca      8280
aattgcagtt cgcgcttagc tggataacgc cacggaatga tgtcgtcgtg cacaacaatg      8340
gtgacttcta cagcgcggag aatctcgctc tctccagggg aagccgaagt ttccaaaagg      8400
tcgttgatca aagctcgccg cgttgtttca tcaagcctta cggtcaccgt aaccagcaaa      8460
tcaatatcac tgtgtggctt caggccgcca tccactgcgg agccgtacaa atgtacggcc      8520
agcaacgtcg gttcgagatg gcgctcgatg acgccaacta cctctgatag ttgagtcgat      8580
acttcggcga tcaccgcttc cctcatggta aatgaaagaa agaactaaat actatatttc      8640
actttgaggt ggaaacgtaa caattttttt tattgtcttt ataatattca tattggtttt      8700
tatcgtattt attttatcca tagattataa aaattcataa agaaagacag aatgaataaa      8760
ctcaaattat tacgaatagg tctttctaat gataaataag tatgaattcg gcgaacgtgg      8820
cgagaaagga agggaagaaa gcgaaaggag cgggcgctag ggcgctggca agtgtagcgg      8880
tcacgctgcg cgtaaccacc acacccgccg cgcttaatgc gccgctacag ggcgcgtcgc      8940
gccattcgcc attcaggctg cgcaactgtt gggaagggcg atcggtgcgg gcctcttcgc      9000
tattacgcca gctggcgaaa gggggatgtg ctgcaaggcg attaagttgg gtaacgccag      9060
ggttttccca gtcacgacgt tgtaaaacga cggccagtga attgtaatac gactcactat      9120
agggcgaatt gggtacgaaa tccttcccga tacctcccaa ggaaaatctc gaatttggat      9180
cccaaattga cgggttagtg tgagcttatc catgcggtta tgcactcttt gaataggaat      9240
ccgttttctg aaagatcctg gctttcgtac tttggtgggt ctccgagatc ctttcgatga      9300
cctatgttga agggatatct atctaatccg atcgattgcg taaagcccgc ggtagcaacg      9360
gaaccgggga agtatacag aaaagacagt tcttttctat tatattagta ttttctatta      9420
tattagatat attagactat tatattagat tagtattagt tagtgatccc gacttagtga      9480
gtctgatgaa ttgttggcac cagtcctaca ttttgtctct gtggaccgag gagaaaaggg      9540
gctcggcggg aagaggagtg taccatgaga gaagcaagga ggtcaacctc tttcaaatat      9600
acaacatgga ttctggcaat gtagttggac tctcatgtcg atccgaatga atcatccttt      9660
ccacggaggt aaatctttgc ctgctaggca agaggatagc aagttccaaa ttctgtctcg      9720
gtaggacatg tatttctatt actatgaaat tcataaatga agtagttaat ggtagggtta      9780
ccattatcct ttttgtagtg acgaatcttg tatgtgttcc taagaaaagg aatttgtcca      9840
tttttcgggg tctcaaaggg gcgtggaaac gcataagaac tcttgaatgg aaaagagatg      9900
taactccagt tccttcggaa tcggtagtca atcctatttc cgataggggc agttgacaat      9960
tgaatccgat tttgaccatt attttcatat ccgtaatagt gcgactgcag a             10011
```

<210> SEQ ID NO 20
<211> LENGTH: 34
<212> TYPE: DNA
<213> ORGANISM: artificial sequence
<220> FEATURE:
<223> OTHER INFORMATION: top strand primer
<220> FEATURE:
<221> NAME/KEY: misc_feature
<222> LOCATION: (1)..(34)

<400> SEQUENCE: 20

```
gccagaattc accacgatcg aacgggaatg gata                              34

<210> SEQ ID NO 21
<211> LENGTH: 28
<212> TYPE: DNA
<213> ORGANISM: artificial sequence
<220> FEATURE:
<223> OTHER INFORMATION: bottom strand primer maize 16S NEP-PEP
<220> FEATURE:
<221> NAME/KEY: misc_feature
<222> LOCATION: (1)..(28)

<400> SEQUENCE: 21
ctctagagat tcggaattgt ctttcctt                                    28

<210> SEQ ID NO 22
<211> LENGTH: 37
<212> TYPE: DNA
<213> ORGANISM: artificial sequence
<220> FEATURE:
<223> OTHER INFORMATION: top strand primer bacteriophage T3 gene 5'UTR
<220> FEATURE:
<221> NAME/KEY: misc_feature
<222> LOCATION: (1)..(37)

<400> SEQUENCE: 22
gaagatgcca tggattaaat ctcctaagtt attaaag                          37

<210> SEQ ID NO 23
<211> LENGTH: 37
<212> TYPE: DNA
<213> ORGANISM: artificial sequence
<220> FEATURE:
<223> OTHER INFORMATION: bottom strand primer bacteriophage T3 5'UTR
<220> FEATURE:
<221> NAME/KEY: misc_feature
<222> LOCATION: (1)..(37)

<400> SEQUENCE: 23
cgaatctctt cccgggtaga gggagacctc atctttg                          37

<210> SEQ ID NO 24
<211> LENGTH: 38
<212> TYPE: DNA
<213> ORGANISM: artificial sequence
<220> FEATURE:
<223> OTHER INFORMATION: top strand primer maize 16S NEP-PEP (RTK38)
<220> FEATURE:
<221> NAME/KEY: misc_feature
<222> LOCATION: (1)..(38)

<400> SEQUENCE: 24
ctccctctac ccgggaagag attcggaatt gtctttcc                         38

<210> SEQ ID NO 25
<211> LENGTH: 38
<212> TYPE: DNA
<213> ORGANISM: artificial sequence
<220> FEATURE:
<223> OTHER INFORMATION: bottom strand primer  (RTK37)
<220> FEATURE:
<221> NAME/KEY: misc_feature
<222> LOCATION: (1)..(38)

<400> SEQUENCE: 25
cgcttagtca tgataaaatc ttggtttatt taatcatc                         38
```

```
<210> SEQ ID NO 26
<211> LENGTH: 85
<212> TYPE: DNA
<213> ORGANISM: Bacteriophage X2

<400> SEQUENCE: 26
aattcgttaa agaatgtagc tgactgcata cttaaaccac ccatactagt tgctgggtgg      60
tttttatgtt ataatataaa tgtgt                                           85

<210> SEQ ID NO 27
<211> LENGTH: 85
<212> TYPE: DNA
<213> ORGANISM: bacteriophage X2

<400> SEQUENCE: 27
ctagacacat ttatattata acataaaaac cacccagcaa ctagtatggg tggtttaagt      60
atgcagtcag ctacattctt taacg                                           85

<210> SEQ ID NO 28
<211> LENGTH: 28
<212> TYPE: DNA
<213> ORGANISM: artificial sequence
<220> FEATURE:
<223> OTHER INFORMATION: top strand primer kpvI gene 10 5'UTR
<220> FEATURE:
<221> NAME/KEY: misc_feature
<222> LOCATION: (1)..(28)

<400> SEQUENCE: 28
gttctagaga cattacgttc tccccttg                                        28

<210> SEQ ID NO 29
<211> LENGTH: 29
<212> TYPE: DNA
<213> ORGANISM: artificial sequence
<220> FEATURE:
<223> OTHER INFORMATION: bottom strand primer kpvI gene 10 5' UTR
<220> FEATURE:
<221> NAME/KEY: misc_feature
<222> LOCATION: (1)..(29)

<400> SEQUENCE: 29
agatatccat ggtgaatctc ctgttgatt                                       29
```